(12) United States Patent
Washburn et al.

(10) Patent No.: US 7,989,433 B2
(45) Date of Patent: Aug. 2, 2011

(54) SUBSTITUTED THIENO[3,2-D]PYRIMIDINES AS MELANIN CONCENTRATING HORMONE RECEPTOR-1 ANTAGONISTS

(75) Inventors: William N. Washburn, Titusville, NJ (US); Pratik Devasthale, Plainsboro, NJ (US); Jeffrey A. Robl, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/473,346

(22) Filed: May 28, 2009

(65) Prior Publication Data

US 2009/0298794 A1 Dec. 3, 2009

Related U.S. Application Data

(60) Provisional application No. 61/056,949, filed on May 29, 2008.

(51) Int. Cl.
| | |
|---|---|
| A61K 31/695 | (2006.01) |
| A61K 31/6615 | (2006.01) |
| A61K 31/661 | (2006.01) |
| A61K 31/519 | (2006.01) |
| C07D 295/04 | (2006.01) |
| C07F 7/10 | (2006.01) |
| C07F 9/06 | (2006.01) |
| C07F 9/09 | (2006.01) |

(52) U.S. Cl. ......... 514/63; 514/260.1; 514/81; 544/278; 544/229

(58) Field of Classification Search .................. 544/278; 514/260.1
See application file for complete search history.

(56) References Cited

U.S. PATENT DOCUMENTS

| | | |
|---|---|---|
| 3,674,836 A | 7/1972 | Creger |
| 3,983,140 A | 9/1976 | Endo et al. |
| 4,027,009 A | 5/1977 | Grier et al. |
| 4,231,938 A | 11/1980 | Monaghan et al. |
| 4,346,227 A | 8/1982 | Terahara et al. |
| 4,379,785 A | 4/1983 | Weyer et al. |
| 4,448,784 A | 5/1984 | Glamkowski et al. |
| 4,450,171 A | 5/1984 | Hoffman et al. |
| 4,499,289 A | 2/1985 | Baran et al. |
| 4,613,610 A | 9/1986 | Wareing |
| 4,639,436 A | 1/1987 | Junge et al. |
| 4,647,576 A | 3/1987 | Hoefle et al. |
| 4,681,893 A | 7/1987 | Roth |
| 4,686,237 A | 8/1987 | Anderson |
| 4,759,923 A | 7/1988 | Buntin et al. |
| 4,871,721 A | 10/1989 | Biller |
| 4,904,769 A | 2/1990 | Rauenbusch |
| 4,924,024 A | 5/1990 | Biller |
| 5,006,530 A | 4/1991 | Angerbauer et al. |
| 5,011,930 A | 4/1991 | Fujikawa et al. |
| 5,177,080 A | 1/1993 | Angerbauer et al. |
| 5,260,440 A | 11/1993 | Hirai et al. |
| 5,273,995 A | 12/1993 | Roth |
| 5,354,772 A | 10/1994 | Kathawala |
| 5,385,929 A | 1/1995 | Bjorge et al. |
| 5,434,150 A | 7/1995 | Austel et al. |
| 5,447,954 A | 9/1995 | Gribble et al. |
| 5,488,064 A | 1/1996 | Sher |
| 5,491,134 A | 2/1996 | Sher et al. |
| 5,506,219 A | 4/1996 | Robl |
| 5,541,204 A | 7/1996 | Sher et al. |
| 5,594,016 A | 1/1997 | Ueno et al. |
| 5,612,359 A | 3/1997 | Murugesan |
| 5,686,104 A | 11/1997 | Mills et al. |
| 5,691,322 A | 11/1997 | Robl |

(Continued)

FOREIGN PATENT DOCUMENTS

DE 196 22 222 4/1997

(Continued)

OTHER PUBLICATIONS

Arnold, Z. et al., "Synthetic Reactions of Dimethylformamide. XXVII. A Simple Synthesis of Aminomalonaldehyde Derivatives", Collection Czechoslov. Chem. Commun., vol. 38, pp. 2633-2640 (1973).
Beccalli, E.M. et al., "Pd-catalyzed intramolecular cyclization of pyrrolo-2-carboxamides: regiodivergent routes to pyrrolo-pyrazines and pyrrolo-pyridines", Tetrahedron, vol. 61, pp. 1077-1082 (2005).
Bergman, J. et al., "Synthesis of Indoles via Ring Closure of 2-Alkylnitroaniline Derivatives", Tetrahedron, vol. 46, No. 17, pp. 6085-6112 (1990).

(Continued)

*Primary Examiner* — Susanna Moore
(74) *Attorney, Agent, or Firm* — Burton Rodney; Maureen S. Gibbons; Jing G. Sun

(57) ABSTRACT

The present invention provides compounds having the following Formula IA and IB, which are useful as MCHR1 antagonists, and includes prodrugs and pharmaceutically acceptable salts thereof:

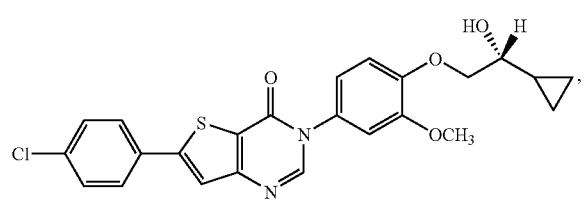

IA

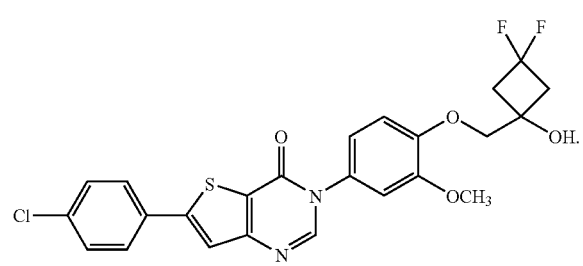

IB

18 Claims, No Drawings

U.S. PATENT DOCUMENTS

| | | | |
|---|---|---|---|
| 5,698,527 | A | 12/1997 | Kim |
| 5,712,396 | A | 1/1998 | Magnin et al. |
| 5,753,675 | A | 5/1998 | Wattanasin |
| 5,770,615 | A | 6/1998 | Cheng et al. |
| 5,776,983 | A | 7/1998 | Washburn et al. |
| 5,990,145 | A | 11/1999 | Wehner et al. |
| 6,011,045 | A | 1/2000 | Wehner et al. |
| 6,043,265 | A | 3/2000 | Murugesan et al. |
| 6,414,002 | B1 | 7/2002 | Cheng et al. |
| 6,482,821 | B2 | 11/2002 | Wehner et al. |
| 7,553,836 | B2 | 6/2009 | Zhao |
| 7,745,447 | B2 | 6/2010 | Washburn et al. |
| 2007/0093509 | A1 | 4/2007 | Washburn et al. |

FOREIGN PATENT DOCUMENTS

| | | |
|---|---|---|
| EP | 0 142 146 | 5/1985 |
| EP | 0 221 025 | 5/1987 |
| EP | 0 531 883 | 3/1993 |
| EP | 0 675 714 | 10/1995 |
| EP | 0 818 448 | 1/1998 |
| EP | 0 992 496 | 4/2000 |
| EP | 1 022 272 | 7/2000 |
| FR | 2 596 393 | 10/1987 |
| GB | 2 205 837 | 12/1988 |
| GB | 2 304 106 | 3/1997 |
| JP | 54-32794 | 10/1979 |
| WO | WO 86/03488 | 6/1986 |
| WO | WO 94/15592 | 7/1994 |
| WO | WO 95/15954 | 6/1995 |
| WO | WO 97/21993 | 6/1997 |
| WO | WO 97/35576 | 10/1997 |
| WO | WO 97/48701 | 12/1997 |
| WO | WO 98/49899 | 11/1998 |
| WO | WO 99/00353 | 1/1999 |
| WO | WO 00/01389 | 1/2000 |
| WO | WO 00/15201 | 3/2000 |
| WO | WO 00/30665 | 6/2000 |
| WO | WO 00/38722 | 7/2000 |
| WO | WO 00/39077 | 7/2000 |
| WO | WO 00/50574 | 8/2000 |
| WO | WO 00/73288 | 12/2000 |
| WO | WO 02/10146 | 2/2002 |
| WO | WO 02/101146 | 12/2002 |
| WO | WO 03/033476 | 4/2003 |
| WO | WO 03/035624 | 5/2003 |
| WO | WO 2004/058762 | 7/2004 |
| WO | WO 2004/092181 | 10/2004 |
| WO | WO 2005/023782 | 3/2005 |
| WO | WO 2005/042541 | 5/2005 |
| WO | WO 2005/047293 | 5/2005 |
| WO | WO 2005/103039 | 11/2005 |
| WO | WO 2005/105805 | 11/2005 |
| WO | WO 2007/050723 | 5/2007 |
| WO | WO 2007/050726 | 5/2007 |

OTHER PUBLICATIONS

Berlin, A. et al., "3-Alkylthiopyrroles: Synthesis and Oxidative Polymerization to Conductive Materials", J. Chem. Soc. Perkin Trans. 2, pp. 699-704 (1990).

Biller, S.A. et al., "Isoprenoid (Phosphinylmethyl)phosphonates as Inhibitors of Squalene Synthetase", Journal of Medicinal Chemistry, vol. 31, No. 10, pp. 1869-1871 (1988).

Biller, S.A. et al., "Squalene Synthase Inhibitors", Current Pharmaceutical Design, vol. 2, No. 1, pp. 1-40 (1996).

Boatman, R.J. et al., "Some Novel Reactions of Pyrrolecarboxylic Acid Chlorides", J. Org. Chem., vol. 41, No. 18, pp. 3050-3051 (1976).

Borowsky, B. et al., "Antidepressant, anxiolytic and anorectic effects of a melanin-concentrating hormone-1 receptor antagonist", Nature Medicine, vol. 8, No. 8, pp. 825-830 (2002).

Brimble, M.A. et al., "Synthesis of 2-Methylpyrrolo[1,2-*a*]pyrazin-1(2*H*)-one", Aust. J. Chem., vol. 41, pp. 1583-1590 (1988).

Budhram, R.S. et al., "$^{13}$C NMR Spectra of 2,3-Dihydro-1*H*-pyrrolo[1,2-*c*]imidazol-1,3-dione and its Thione Analogues", Organic Magnetic Resonance, vol. 13, No. 2, pp. 89-91 (1980).

Capson, T.L., "Synthesis and Evaluation of Ammonium Analogs of Carbocationic Intermediates in Squalene Biosynthesis", dissertation, Department of Medicinal Chemistry, University of Utah, pp. iv-v, Table of Contents, 16-17, 40-43, 48-51, Summary (Jun. 1987).

Carpenter, A.J. et al., "Novel benzimidazole-based MCH R1 antagonists", Bioorganic & Medicinal Chemistry Letters, vol. 16, pp. 4994-5000 (2006).

Corey, E.J. et al., "Application of Unreactive Analogs of Terpenoid Pyrophosphates to Studies of Multistep Biosynthesis. Demonstration That 'Presqualene Pyrophosphate' Is an Essential Intermediate on the Path to Squalene", Journal of the American Chemical Society, vol. 98, No. 5, pp. 1291-1293 (1976).

Focella, A. et al., "The Synthesis of Two Phenacetin Metabolites", Canadian Journal of Chemistry, vol. 50, pp. 2025-2030 (1972).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16, No. 1, pp. 16-30 (1998).

Gupton, J.T. et al., "Application of 2-Substituted Vinamidinium Salts to the Synthesis of 2,4-Disubstituted Pyrroles", J. Org. Chem. vol. 55, No. 15, pp. 4735-4740 (1990).

Handy, S.T. et al., "An unusual dehalogenation in the Suzuki coupling of 4-bromopyrrole-2-carboxylates", Tetrahedron Letters, vol. 44, pp. 427-430 (2003).

Hara, S., "Ileal Na$^+$/bile acid cotransporter inhibitors", Drugs of the Future, vol. 24, No. 4, pp. 425-430 (1999).

Hertzog, D.L. et al., "The discovery and optimization of pyrimidinone-containing MCH R1 antagonists", Bioorganic & Medicinal Chemistry Letters, vol. 16, pp. 4723-4727 (2006).

Iwanowicz, E.J. et al., "Inhibitors of Inosine Monophosphate Dehydrogenase: SARs about the *N*-[3-Methoxy-4-(5-oxazolyl)phenyl Moiety", Bioorganic & Medicinal Chemistry Letters, vol. 13, pp. 2059-2063 (2003).

Jabin, I. et al., "Reaction of Cyclohexanone Benzylimines with Ethylidenemalonate Diesters. Diphenyl 2-Ehtylidenemalonate: A Highly Electrophilic Synthetic Equivalent of Crotonic Esters", J. Org. Chem., vol. 66, No. 1, pp. 256-261 (2001).

Katritzky, A.R. et al., "Novel Synthesis of Bicycles with Fused Pyrrole, Indole, Oxazole, and Imidazole Rings", J. Org. Chem., vol. 69, No. 26, pp. 9313-9315 (2004).

Kowalski, T.J. et al., "Melanin-concentrating hormone-1 receptor antagonism decreases feeding by reducing meal size", European Journal of Pharmacology, vol. 497, pp. 41-47 (2004).

Kowalski, T.J. et al., "Therapeutic potential of melanin-concentrating hormone-1 receptor antagonists for the treatment of obesity", Expert Opin. Investig. Drugs, vol. 13, No. 9, pp. 1113-1122 (2004).

Krause, B.R. et al., Chapter 6: "ACAT Inhibitors: Physiologic Mechanisms for Hypolipidemic and Anti-Atherosclerotic Activities in Experimental Animals", Inflammation: Mediators and Pathways, CRC Press, Inc., publ., Ruffolo, Jr., R.R. et al., eds., pp. 173-198 (1995).

Laxmi, Y.R.S. et al., "Chemoenzymatic Synthesis of Methyl (6*S*)-(—)-6,8-Dihydroxyoctanoate: A Precursor to (*R*)-(+)-α-Lipoic Acid", Synthesis, pp. 594-596 (1996).

Ljung, B. et al., "AZ 242, a novel PPARα/γ agonist with beneficial effects on insulin resistance and carbohydrate and lipid metabolism in ob/ob mice and obese Zucker rats", Journal of Lipid Research, vol. 43, pp. 1855-1863 (2002).

McClard, R.W. et al., "Novel Phosphonylphosphinyl (P-C-P-C-) Analogues of Biochemically Interesting Diphosphates. Syntheses and Properties of P-C-P-C- Analogues of Isopentenyl Diphosphate and Dimethylallyl Diphosphate", J. Am. Chem. Soc., vol. 109, pp. 5544-5545 (1987).

Negoro, T. et al., "Novel, Highly Potent Aldose Reductase Inhibitors: (*R*)-(—)-2-(4-Bromo-2-fluorobenzyl)-1,2,3,4-tetrahydropyrrolo[1,2-*a*]pyrazine-4-spiro-3'-pyrrolidine-1,2',3,5'-tetrone (AS-3201) and Its Congeners", Journal of Medicinal Chemistry, vol. 41, No. 21, pp. 4118-4129 (1998).

Nicolosi, R.J. et al., "The ACAT Inhibitor, CI-1011 is effective in the prevention and regression of aortic fatty streak area in hamsters", Atherosclerosis, vol. 137, pp. 77-85 (1998).

Ortiz de Montellano, P.R. et al., "Inhibition of Squalene Synthetase by Farnesyl Pyrophosphate Analogues", Journal of Medicinal Chemistry, vol. 20, No. 2, pp. 243-249 (1977).

Papadopoulos, E.P., "Reactions of Phenyl Isothiocyanate with Metal Derivatives of Pyrrole", J. Org. Chem., vol. 31, pp. 3060-3062 (1966).

Papadopoulos, E.P., "Reactions of Pyrrole with Isocyanates. Preparation and Reactions of N-Ethoxycarbonylpyrrole-2-carboxyamide and Pyrrole-1,2-dicarboximide", J. Org. Chem. vol. 37, No. 3, pp. 351-355 (1972).

Papadopoulos, E.P., "Reactions of Pyrrole with Isothiocyanates. Preparation and Reactions of N-Ethoxycarbonylpyrrole-2-thiocarboxamide and 2-Thiopyrrole-1,2-dicarboximide", J. Org. Chem. vol. 38, No. 4, pp. 667-674 (1973).

Papadopoulos, E.P. et al., "Reactions of Phenyl Isocyanate and Phenyl Isothiocyanate with Indole and Metal Derivatives of Indole", J. Org. Chem., vol. 33, No. 12, pp. 4551-4554 (1968).

Papadopoulos, E.P. et al., "Reactions of Phenyl Isocyanate with Some Metal Derivatives of Pyrrole", J. Org. Chem., vol. 31, pp. 327-329 (1966).

Rosenblum, S.B. et al., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235): A Designed, Potent, Orally Active Inhibitor of Cholesterol Absorption", J. Med. Chem., vol. 41, No. 6, pp. 973-980 (1998).

Salisbury, B.G. et al., "Hypocholesterolemic activity of a novel inhibitor of cholesterol absorption, SCH 48461", Atherosclerosis, vol. 115, pp. 45-63 (1995).

Sliskovic, D.R. et al., "ACAT Inhibitors: Potential Anti-atherosclerotic Agents", Current Medicinal Chemistry, vol. 1, No. 3, pp. 204-225 (1994).

Smith, C. et al., "RP 73163: A Bioavailable Alkylsulphinyl-Diphenylimidazole ACAT Inhibitor", Bioorganic & Medicinal Chemistry Letters, vol. 6, No. 1, pp. 47-50 (1996).

Sorbera, L.A. et al., "Avasimibe: Treatment of Lipoprotein Disorders—ACAT Inhibitor", Drugs of the Future, vol. 24, No. 1, pp. 9-15 (1999).

Sosa, A.C.B. et al., "Controlling cyclizations of 2-pyrrolecarboxamidoacetals. Facile solvation of β-amido aldehydes and revised structure of synthetic homolongamide", Tetrahedron Letters, vol. 41, pp. 4295-4299 (2000).

Souers, A.J. et al., "Identification of 2-(4-Benzyloxyphenyl)-N-[1-(2-pyrrolidin-1-yl-ethyl)-1H-indazol-6-yl]acetamide, an Orally Efficacious Melanin-Concentrating Hormone Receptor 1 Antagonist for the Treatment of Obesity", Journal of Medicinal Chemistry, vol. 48, No. 5, pp. 1318-1321 (2005).

Stout, D.M., "Inhibitors of Acyl-CoA:Cholesterol O-Acyl Transferase (ACAT) as Hypocholesterolemic Agents. 6. The First Water-Soluble ACAT Inhibitor with Lipid-Regulating Activity. Inhibitors of Acyl-CoA:Cholesterol Actyltransferase (ACAT). 7. Development of a Series of Substituted N-Phenyl-N'-[(1-phenylcyclopentyl)-methyl]ureas with Enhanced Hypocholestrolemic Activity", Chemtracts-Organic Chemistry, vol. 8, pp. 359-362 (1995).

Takekawa, S. et al., "T-226296: a novel, orally active and selective melanin-concentrating hormone receptor antagonist", European Journal of Pharmacology, vol. 438, pp. 129-135 (2002).

Ulven, T. et al., "6-Acylamino-2-aminoquinolines as Potent Melanin-Concentrating Hormone 1 Receptor Antagonists. Identification, Structure-Activity Relationship, and Investigation of Binding Mode", Journal of Medicinal Chemistry, vol. 48, No. 18, pp. 5684-5697 (2005).

Vippagunta, S.R. et al., "Crystalline solids", Advanced Drug Delivery Reviews, vol. 48, pp. 3-26 (2001).

Warshakoon, N.C. et al., "Design and Synthesis of substituted quinolines as novel and selective melanin concentrating hormone antagonists as anti-obesity agents", Bioorganic & Medicinal Chemistry Letters, vol. 16, pp. 5207-5211 (2006).

Yajima, K. et al., "Combination therapy with PPARγ and PPARα agonists increases glucose-stimulated insulin secretion in db/db mice", Am. J. Physiol. Endocrinol. Metab., vol. 284, pp. E966-E971 (2003).

Yang, Z. et al., "A facile route to N-fused pyrrole lactams", J. Indian Chem. Soc., vol. 80, pp. 790-791 (2003).

Database WPI, AN 2005-242113, Derwent Publications Ltd., London, GB, Mar. 17, 2005.

ScienceDirect, Bioorganic & Medicinal Chemistry Letters, vol. 16, p. 1 (2006).

Office communication from USPTO dated Feb. 25, 2009, U.S. Appl. No. 11/568,255, filed Oct. 25, 2006; First Named Inventor; William N. Washburn.

Office communication from USPTO dated Sep. 29, 2009, U.S. Appl. No. 11/568,255, filed Oct. 25, 2006; First Named Inventor; William N. Washburn.

SUBSTITUTED THIENO[3,2-D]PYRIMIDINES AS MELANIN CONCENTRATING HORMONE RECEPTOR-1 ANTAGONISTS

CROSS-REFERENCE TO RELATED APPLICATIONS

This application claims the benefit of U.S. provisional application Ser. No. 61/056,949, filed on May 29, 2008, the disclosure of which is hereby incorporated by reference in its entirety.

BACKGROUND

Several lines of pharmacological and genetic evidence support the role of melanin concentrating hormone receptor-1 (hereafter "MCHR1") as a modulator of food intake and body weight. Central administration of melanin concentrating hormone (MCH) increases food intake and body weight in both rats and mice. Chronic ICV infusion of MCH causes increased food intake and ultimately obesity in mice, while infusion of an MCH peptide antagonist blocks MCH-induced food intake and results in weight loss and decreased feeding in diet-induced obese mice.

The expression of both the MCH peptide and receptor are modulated by nutritional status. MCH mRNA is upregulated both in hyperphagic obese mice (ob/ob), and fasted animals. Targeted disruption of the gene for MCH peptide results in hypophagia and leanness. Disruption of the MCHR1 gene causes leanness, altered metabolism, and hyperlocomotion accompanied by mild hyperphagia. Conversely, over-expression of MCH peptide results in hyperphagia, obesity and diabetes. Small molecule MCHR1 antagonists have been shown to cause weight loss in rodent weight and feeding models after both oral and intraperitoneal administration; *Eur. J; Pharmacol*, 438:129-135 (2002); *Nat. Med.*, 8:825-830 (2002); *Eur. J. Pharmacol*, 497; 41-47 (2004).

MCHR1 has also been reported to play a key role in the pathogenesis of acute experimental colitis and possibly human IBD (inflammatory bowel disease). It has been shown that immunoneutralization is an effective treatment for TNBS-induced colitis. Kokkotou, E. et al., "Melanin-concentrating hormone as a mediator of intestinal inflammation", *PNAS*, 105(30):10613-10618 (Jul. 29, 2008).

In addition, MCH and MCHR1 has also been reported to play a role in the endocrine and behavioral responses to stress. Treatment of rats and mice with MCHR antagonists produce a robust anti-depressant and anti-anxiolytic effect. (JPET DOI:10.1124/jpet.108.143362)

Numerous non-peptide MCHR1 antagonists have been disclosed. The scope of the genus for each reflects a common perception regarding the criteria required for ligand recognition as MCHR1 agonists. A recent review of MCHR1 patent disclosures emphasized the commonality of these structures by the following description; "Ubiquitous throughout the MCH patent literature are molecules consisting of a central scaffold to which linkers to an aryl or heteroaryl group and a basic amino functionality are attached" (T. J. Kowalski, T. J. et al., *Exp. Opin. Invest. Drugs*, 13:1113-1122 (2004)). Pharmacophore models of these geni consistently envision a presumed prerequisite electrostatic interaction between a basic amine center of the antagonist ligand and aspartic acid 123 of the receptor which presumably is envisaged to emulate the mandatory interaction between arginine 14 of MCH peptide agonists with aspartic acid 123 of the MCHR1 receptor. (Ulven, T. et al., *J. Med. Chem.*, 48:5684-5697 (2005)). However, incorporation of this basic amine in a MCHR1 antagonist increases substantially the probability of binding to off-target ion-channels and biogenic amine receptors.

U.S. Patent Publication No. 2007/0093509 A1 published Apr. 26, 2007 discloses a series of novel high affinity selective MCHR1 antagonists of formula A:

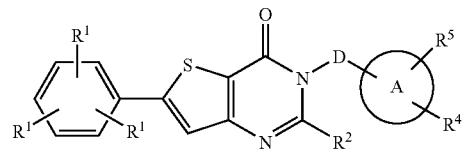

wherein,
A is phenyl or a monocyclic heteroaryl;
D is $CH_2$ or a direct bond;
$R^1$ is independently selected from hydrogen, halogen, lower alkyl, lower cycloalkyl, $CF_3$, $OR^6$ or $SR^6$;
$R^2$ is hydrogen or lower alkyl;
$R^4$ is hydroxyl or G-$D^2$-$Z_n$;
n is an integer from 1 to 3;
$R^5$ is hydrogen, halogen, lower alkyl, lower cycloalkyl, $CF_3$, $SR^6$, lower alkoxy, lower cycloalkoxy, CN, $CONR^7R^7$, $SOR^6$, $SO_2R^6$, $NR^7COR^7$, $NR^7CO_2R^7$, $CO_2R^6$, heteroaryl, $NR^7SO_2R^6$ or $COR^6$;
G is O, S or $CR^7R^7$;
$D^2$ is a direct bond, lower alkyl, lower cycloalkyl or a 4 to 6-membered non-basic heterocycle;
Z is hydrogen, hydroxyl, lower alkoxy, lower cycloalkoxy, $OCONR^7R^7$, CN, $CONR^7R^7$, $SOR^6$, $SO_2R^6$, $NR^7COR^7$, $NR^7CO_2R^7$, $CO_2R^6$, heteroaryl, $NR^6SO_2R^6$ or $COR^6$;
$R^6$ is independently selected from lower alkyl or lower cycloalkyl; and
$R^7$ is independently selected from hydrogen, lower alkyl or lower cycloalkyl, wherein two $R^7$ and the atom to which they are attached may optionally form a ring of 4 to 7 atoms.

SUMMARY OF THE INVENTION

The present invention is directed to MCHR1 antagonists having surprisingly superior pharmacodynamic, pharmacokinetic and safety profiles, such as those having the following formula IA or IB, including all stereoisomers thereof:

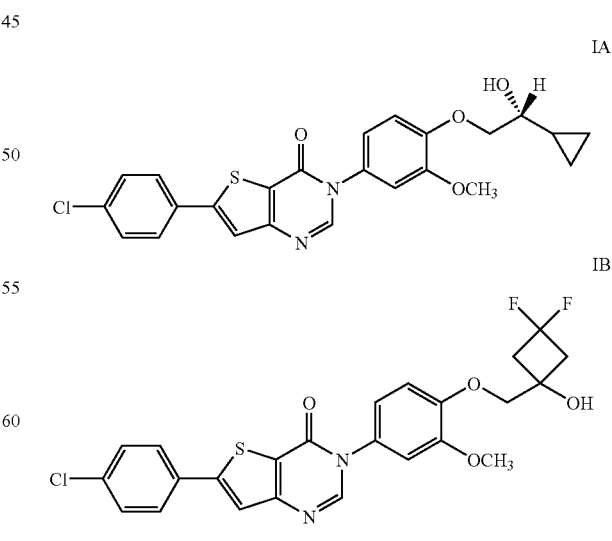

or prodrugs or pharmaceutically acceptable salts thereof. Preferred prodrugs of the formula IA are in the form of prodrug esters or salts thereof selected from the group consisting of acetate, pivalate, methylcarbonate, benzoate, phosphate, and amino acid ester; or in the form of a prodrug ethers or salts thereof selected from the group consisting of phosphate acetal and O-glucoside.

Some preferred prodrug ester groups having the following formula:

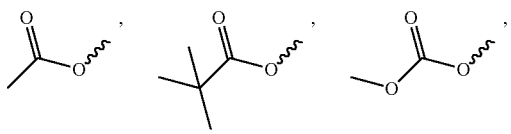

wherein y is 1 to 4 and the prodrug ether is

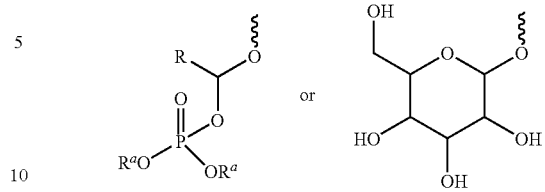

wherein R is alkyl or hydrogen and $R^a$ is H, alkyl or benzyl.

According to one aspect of the present invention, compounds are provided having one of the following structures, including stereoisomers thereof;

IA¹

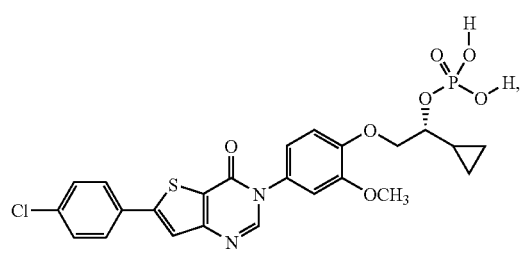

IA²

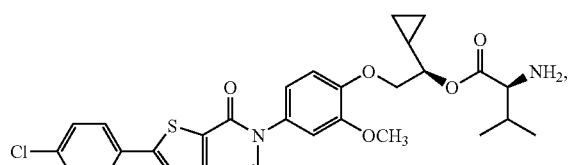

IA³

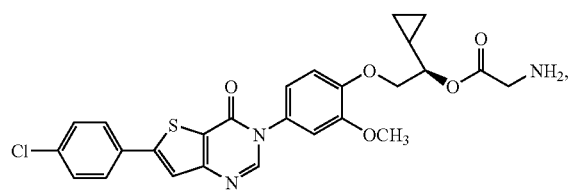

IA⁴

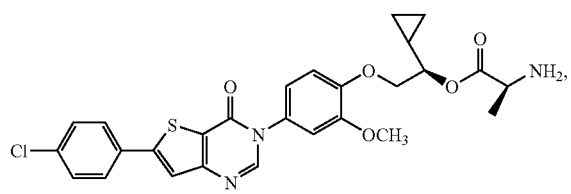

IA⁵

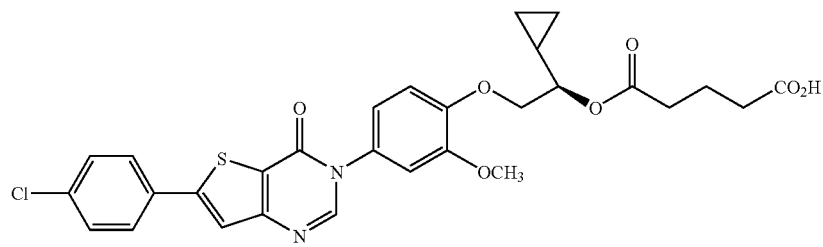

-continued

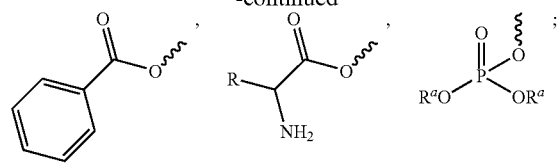

wherein $R^a$ is H, alkyl, benzyl or

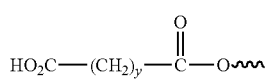

including a pharmaceutically acceptable salts of any of the foregoing structures.

According to one aspect of the present invention, compounds are provided having the e following structure IB, including all stereoisomers thereof:

IB

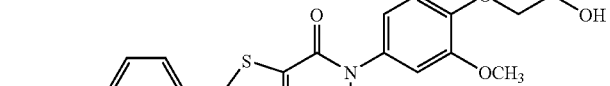

or a prodrug or pharmaceutically acceptable salt thereof.

Preferred prodrugs of compounds of formula IB are in the form of esters or salts thereof selected from the group consisting of acetate, pivalate, methylcarbonate, benzoate, phosphate, and amino acid ester; or in the form of prodrug ethers or salts thereof selected from the group consisting of phosphate acetal and O-glucoside.

According to one aspect of the present invention, the prodrug ester of formula IB is one of the following

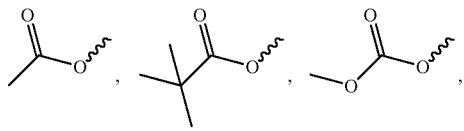

wherein y is 1 to 4 and the prodrug ether is

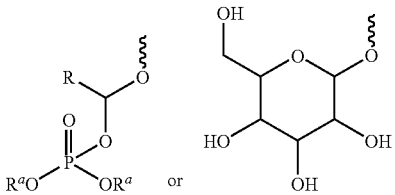

wherein R is alkyl or hydrogen and $R^a$ is H, alkyl or benzyl.

Preferred compounds of formula IB have one of the following structures, including stereoisomers thereof:

IB¹

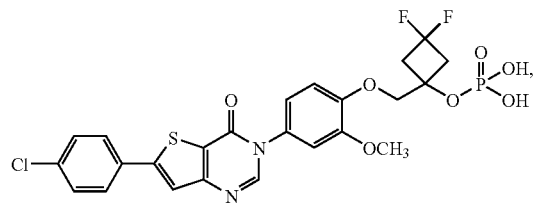

IB²

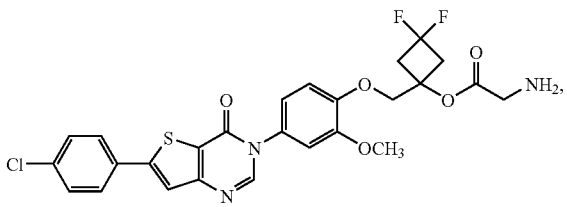

IB³

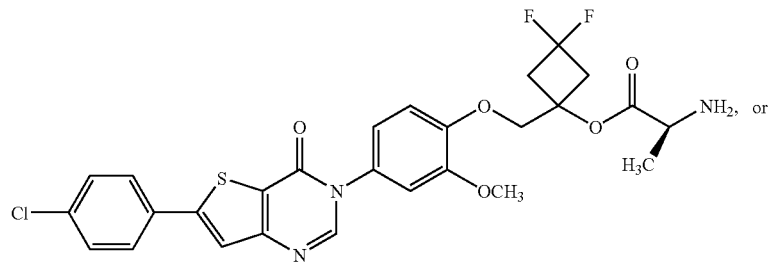

IB⁴

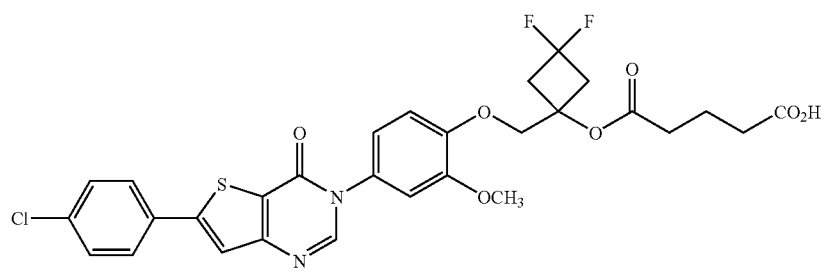

-continued

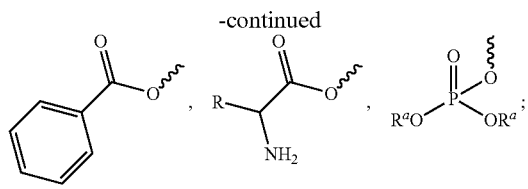

wherein $R^a$ is H, alkyl, benzyl or

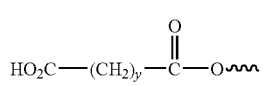

or may be pharmaceutically acceptable salt of any of the foregoing structures.

According to one aspect of the present invention, pharmaceutical compositions are provided comprising at least one compound according to formula IA or IB as described herein, and may optionally include at least one additional therapeutic agent selected from the group consisting of anti-obesity agents; anti-diabetic agents, appetite suppressants; cholesterol/lipid-lowering agents, and HDL-raising agents together with at least one pharmaceutically acceptable diluent or carrier.

According to one aspect of the present invention, pharmaceutical combinations are provided comprising at least one compound according to formula IA or IB and at least one additional therapeutic agent selected ftom the group consisting of anti-obesity agents; anti-diabetic agents, appetite suppressants; cholesterol/lipid-lowering agents, and HDL-raising agents.

Preferred pharmaceutical combinations of the present invention comprise a compound of formula IA or IB, or prodrugs thereof or salts thereof, and an anti-diabetic agent or an antiobesity agent.

The present invention is also directed to the use of compound having formula IA or IB, (or a prodrug thereof), in the manufacture of a medicament that is useful for treating obesity, diabetes, anxiety, depression or inflammatory bowel disease.

The present invention is further directed to compounds having one of the following formula:

The present invention is further directed to a process for the enzymatic reduction of a ketone of the structure

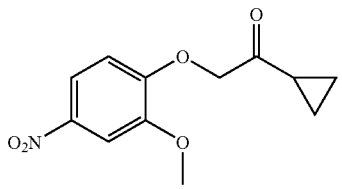

a)
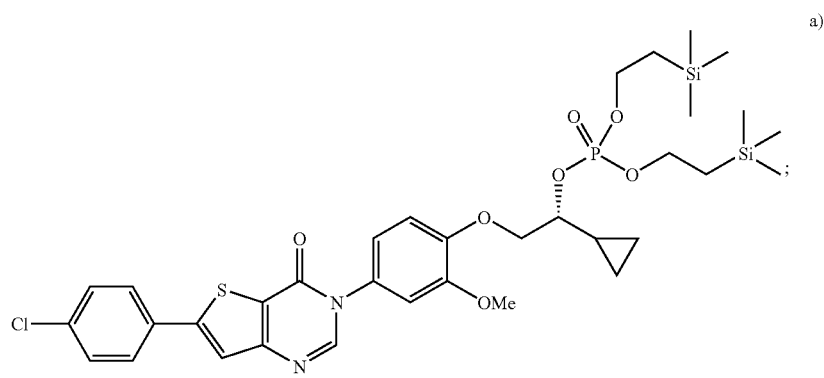

b)
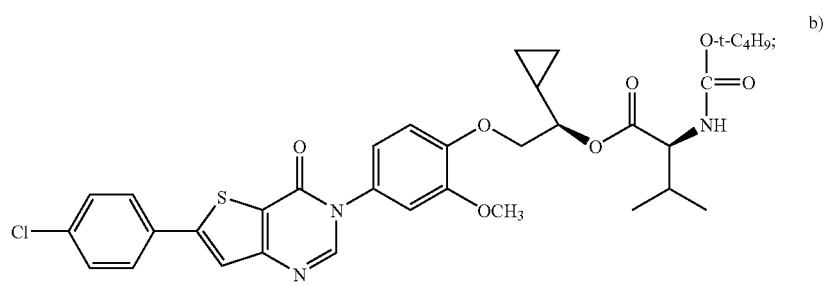

c)
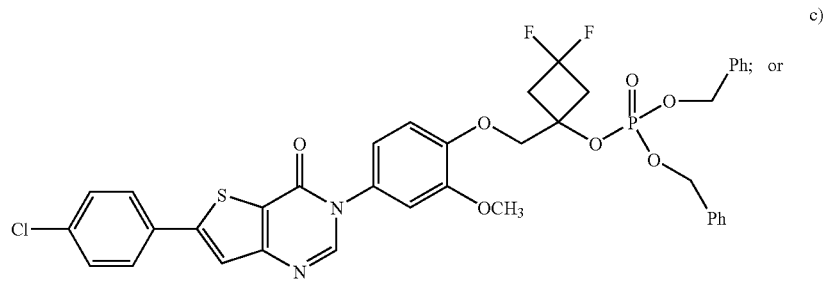

d)
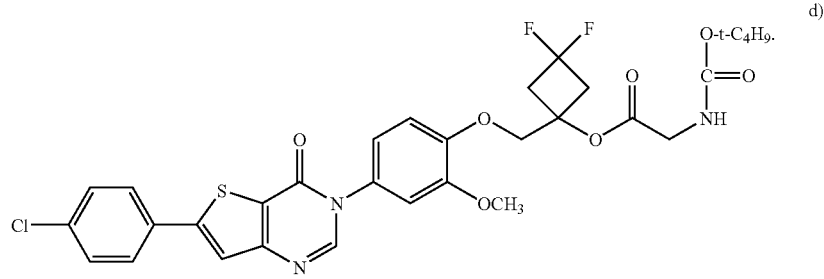

Example 1

Part B Ketone to an alcohol of the structure

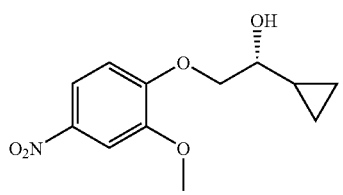

Example 1

Part C (R)-Alcohol, which comprises reacting the ketone with a ketoreductase enzyme to convert the ketone to the alcohol.

In one preferred embodiment, ketoreductase enzyme is ketoreductase (KRED)-112 or ketoreductase (KRED)-113 or a ketoreductase that is produced from *Candida sonorensis* SC16117 (ATCC® #56511).

According to one aspect of the present inventions a process for preparing a compound of formula IA is provided

IA

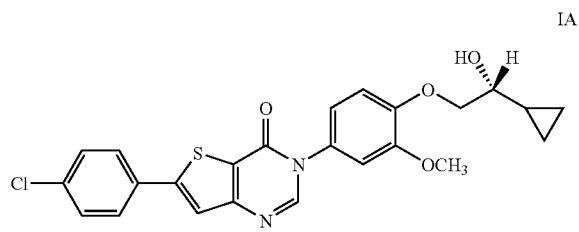

which comprises enzymatically reducing a compound of the structure

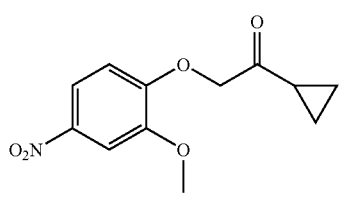

employing ketoreductase-112 or ketoreductase-113, or the microbial strain *Candida sonorensis* SC16117 (ATCC® #56511), to form the (R)-alcohol of the structure

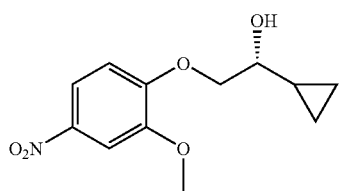

and condensing the above (R)-alcohol with a compound of the structure

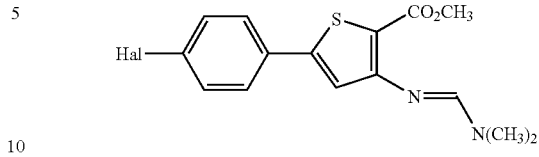

in the presence of an organic solvent to form the formula IA compound.

DETAILED DESCRIPTION OF THE INVENTION

Definitions

Unless otherwise indicated, the term "lower alkyl" as employed herein alone or as part of another group includes both straight and branched chain hydrocarbons containing 1 to 8 carbons, and the terms "alkyl" and "alk" as employed herein alone or as part of another group includes both straight and branched chain hydrocarbons containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, alkynyl, cycloalkyl, cycloalkenyl, cycloalkylalkyl, cycloalkylalkyloxy, hydroxy, hydroxyalkyl, acyl, alkanoyl, heteroaryl, heteroaryloxy, cycloheteroalkyl, arylheteroaryl, arylalkoxycarbonyl, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, any one of which may optionally be a spiro substituted cycloalkyl, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

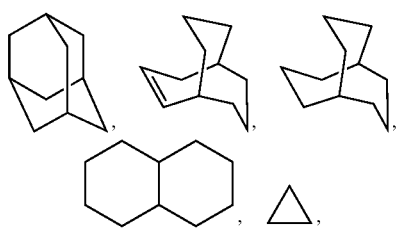

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, nitro, cyano, thiol and/or alkylthio and/or any of the alkyl substituents.

The term "halogen" or "halo" as used herein alone or as part of another group refers to chlorine, bromine, fluorine, and iodine, and $CF_3$, with chlorine or fluorine being preferred.

The term "metal ion" refers to alkali metal ions such as sodium, potassium or lithium and alkaline earth metal ions such as magnesium and calcium, as well as zinc and aluminum.

The term "prodrug" encompasses both the term "prodrug esters" and the term "prodrug ethers" and can include pharmaceutically acceptable salts thereof. The term "prodrug esters" as employed herein includes esters and carbonates formed by reacting one or more hydroxyls of compounds of the present invention with either alkyl, alkoxy, or aryl substituted acylating agents or phosphorylating agent employing procedures known to those skilled in the art to generate acetates, pivalates, methylcarbonates, benzoates, amino acid esters, phosphates and the like.

Examples of such prodrug esters include

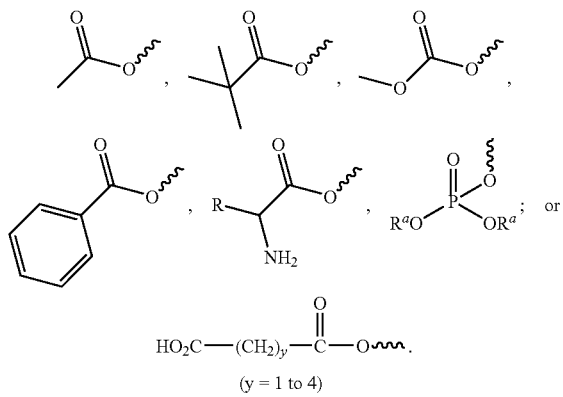

The term "prodrug ethers" include both phosphate acetals and O-glucosides. Representative examples of such prodrug ethers include

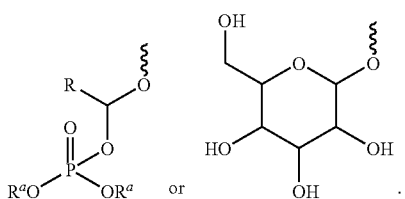

In the above formulae, R is alkyl or H, and $R^a$ is H, alkyl or benzyl.

Salts and Stereoisomers

The compounds of the invention (including compounds IA and IB) when in the form of prodrugs can be present as salts, which are also within the scope of this invention. Pharmaceutically acceptable (i.e., non-toxic, physiologically acceptable) salts are preferred. If the compounds of the present invention have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of the present invention having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of the present invention or their pharmaceutically acceptable salts, are also included.

Preferred salts of the compounds of the present invention which contain a basic group include monohydrochloride, hydrogensulfate, methanesulfonate, phosphate, nitrate or acetate.

Preferred salts of the compounds of the present invention which contain an acid group include sodium, potassium and magnesium salts and pharmaceutically acceptable organic amines.

All stereoisomers of the compounds of the present invention are contemplated, either in admixture or in pure or substantially pure form. The compounds of the present invention can have asymmetric centers at any of the carbon atoms including any one of the substituents. Consequently, compounds of the present invention can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

Pharmaceutical Compositions and Combinations

According to some embodiments of the present invention, pharmaceutical compositions are provided, comprising at least one compound as described herein, and at least one pharmaceutically acceptable diluent or carrier. The pharmaceutical compositions of the present invention may optionally include at least one additional therapeutic agent selected from the group consisting of anti-obesity agents; anti-diabetic agents, antidepressant agents, anti-anxiety agents, anti-inflammatory agents, appetite suppressants; cholesterol/lipid-lowering agents, and HDL-raising agents, and other therapeutic agents as defined herein.

The present invention is also directed to pharmaceutical combinations, comprising at least one compound of the present invention, and at least one additional therapeutic agent, selected from the group consisting of anti-obesity agents; anti-diabetic agents, antidepressant agents, anti-anxiety agents, anti-inflammatory agents, appetite suppressants; cholesterol/lipid-lowering agents, and HDL-raising agents, and other therapeutic agents as defined herein.

According to one embodiment of the present invention, the anti-diabetic agent is selected from the group consisting of insulin secretagogues, insulin sensitizers, glucokinase inhibitors, glucocorticoid antagonist, fructose 1,6-bis phosphatase inhibitors, AMP kinase activators, incretin modulators glucosidase inhibitors, aldose reductase inhibitors PPAR γ agonists, PPAR α agonists, PPAR δ antagonists or agonists, PPAR α/γ dual agonists, 11-β-HSD-1 inhibitors, dipeptidyl peptidase IV (DP4) inhibitors, SGLT2 inhibitors, such as dapagliflozin, insulin, glucagon-like peptide-1 (GLP-1), GLP-1 agonists, and PTP-1B inhibitors.

According to one embodiment of the present invention, the additional therapeutic agent is an antiobesity agent. Examples of suitable anti-obesity agents for use in combination with the compounds of the present invention include melanocortin receptor (MC4R) agonists, cannabinoid receptor modulators, endocannabinoid synthesis modulators, GPR119 agonists, inhibitors of fat absorption, growth hormone secretagogue receptor (GHSR) antagonists, galanin receptor modulators, orexin antagonists, SGLT2 inhibitors, DPP4 inhibitors, triple monoamine reuptake inhibitors, CCK agonists, GLP-1 agonists, and other Pre-proglucagon-derived peptides; NPY1 or NPY5 antagonist, NPY2 and NPY4 modulators, corticotropin releasing factor modulators, histamine receptor-3 (H3) modulators, aP2 inhibitors, PPAR gamma modulators, PPAR delta modulators, acetyl-CoA carboxylase (ACC) inhibitors, steroyl Co-A desaturase-1 (SCD-1) inhibitors, 11-β-HSD-1 inhibitors, adinopectin receptor modulators; beta 3 adrenergic agonists, thyroid receptor beta modulators, lipase inhibitors, serotonin receptor agonists, monoamine reuptake inhibitors or releasing agents, anorectic agents, CNTF (ciliary neurotrophic factor), BDNF (brain-derived neurotrophic factor), leptin and leptin receptor modulators, cannabinoid-1 receptor inverse agonists/neutral antagonists, DGAT inhibitors, opiate antagonists, and amylin receptor modulators.

Preferred antiobesity agents include SGLT2 inhibitors, such as those disclosed in U.S. Pat. No. 6,414,126. Most preferred anti-obesity agents include dapagliflozin and lipase inhibitors, such as orlistat, or monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamnphetamine, phentermine, phenylpropanolamine or mazindol.

Methods of Use

According to one embodiment of the present invention, methods are provided for treating obesity in a patient in need of such treatment, comprising administering a therapeutically effective amount of at least one compound according to the present invention alone or in combination with one or more additional antiobesity agents, wherein the obesity agent is selected from those described herein.

According to one embodiment of the present invention, methods are provided for treating diabetes, especially Type II diabetes, in a patient in need of such treatment, comprising administering a therapeutically effective amount of at least one compound according to The present invention alone or in combination with one or more additional antidiabetic agents, wherein the diabetic agent is described herein.

According to one embodiment of the present invention, methods for treating depression in a patient are provided, comprising administering a therapeutically effective amount of at least one compound according to The present invention.

According to one embodiment of the present invention, methods are provided for treating anxiety in a patient in need of such treatment, comprising administering a therapeutically effective amount of a compound having of the present invention.

According to one embodiment of the present invention, methods are provided for treating inflammatory bowel disease, comprising administering a therapeutically effective amount of at least one compound of the present invention.

Utility

The compounds of the present invention can be administered to mammals, preferably humans, for the treatment of a variety of conditions and disorders, including, but not limited to metabolic and eating disorders as well as conditions associated with metabolic disorders (e.g., obesity, diabetes, arteriosclerosis, hypertension, polycystic ovary disease, cardiovascular disease, osteoarthritis, dermatological disorders, impaired glucose hemostasis, insulin resistance, hypercholesterolemia, hypertriglyceridemia, choletithiasis, dislipidemic conditions, bulimia nervosa and compulsive eating disorders); sleep disorders; and psychiatric disorders, such as depression, anxiety, schizophrenia, substance abuse, cognition-enhancement and Parkinson's disease.

The compounds described in the present invention could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and neurotropic agents (e.g., piracetam, levetiracetain). Examples of suitable therapies for treatment of Alzheimer's disease and cognitive disorders for use in combination with the compounds of the present invention include donepezil, tacrine, revastigraine, 5HT6, gamma secretase inhibitors, beta secretase inhibitors, SK channel blockers, Maxi-K blockers, and KCNQs blockers.

The compounds described in the present invention could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transporter modulators, such as ropinirole, or pramipexole or neurotrophic factors such as glial derived neurotrophic factor (GDNF).

Dosage Forms

The compounds of the present invention can be administered in oral dosage form. The dosage form for said pharmaceutical composition includes such oral dosage forms as granules, powders, tablets, capsules, syrups, emulsions, suspensions, etc. and such non-oral dosage forms as injections (e.g., subcutaneous, intravenous, intramuscular and intraperitoneal injections), drip infusions, external application forms (e.g., nasal spray preparations, transdermal preparations, ointments, etc.), and suppositories (e.g., rectal and vaginal suppositories).

These dosage forms can be manufactured by the per se known technique conventionally used in pharmaceutical procedures. The specific manufacturing procedures are as follows.

To manufacture an oral dosage form, an excipient (e.g., lactose, sucrose, starch, mannitol, etc.), a disintegrator (e.g., calcium carbonate, carboxymethylcellulose calcium, etc.), a binder (e.g., α-starch, gum arabic, carboxymethylcellulose, polyvinylpyrrolidone, hydroxypropylcellulose, etc.), and a lubricant (e.g., talc, magnesium stearate, polyethylene glycol 6000, etc.), for instance, are added to the active component or components and the resulting composition is compressed. Where necessary, the compressed product is coated, by the per se known technique, for masking the taste or for enteric dissolution or sustained release. The coating material that can be used includes, for instance, ethylcellulose, hydroxymethylcellulose, polyoxyethylene glycol, cellulose acetate phthalate, hydroxypropylmethylcellulose phthalate, and EUDRAGIT® (Rohm & Haas, Germany, methacrylic-acrylic copolymer).

Injections can be manufactured typically by the following procedure. The active component or components are dissolved, suspended or emulsified in an aqueous vehicle (e.g., distilled water, physiological saline, Ringer's solution, etc.) or an oily vehicle (e.g., vegetable oil such as olive oil, sesame oil, cottonseed oil, corn oil, etc. or propylene glycol) together with a dispersalt, e.g., Tween 80 (Atlas Powder, U.S.A.), HCO 60 (Nikko Chemicals), polyethylene glycol, carboxymethylcellulose, sodium alginate, etc.), a preservative (e.g., methyl p-hydroxybenzoate, propyl p-hydroxybenzoate, benzyl alcohol, chlorobutanol, phenol, etc.), an isotonizing agent (e.g., sodium chloride, glycerol, sorbitol, glucose, inverted sugar, etc.) and other additives. If desired, a solubilizer (e.g., sodium salicylate, sodium acetate, etc.), a stabilizer (e.g., human serum albumin), a soothing agent (e.g., benzalkonium chloride, procaine hydrochloride, etc.) and other additives can also be added.

A dosage form for external application can be manufactured by processing the active component or components into a solid, semi-solid or liquid composition. To manufacture a solid composition, for instance, the active component or components, either as they are or in admixture with an excipient (e.g., lactose, mannitol, starch, microcrystalline cellulose, sucrose, etc.), a thickener (e.g., natural gums, cellulose derivatives, acrylic polymers, etc.), etc., are processed into powders. The liquid composition can be manufactured in substantially the same manner as the injections mentioned above. The semi-solid composition is preferably provided in a hydrous or oily gel form or an ointment form. These compositions may optionally contain a pH control agent (e.g., carbonic acid, phosphoric acid, citric acid, hydrochloric acid, sodium hydroxide, etc.), and a preservative (e.g., p-hydroxybenzoic acid esters, chlorobutanol, benzalkonium chloride, etc.), among other additives.

Suppositories can be manufactured by processing the active component or components into an oily or aqueous composition, whether solid, semi-solid or liquid. The oleaginous base that can be used includes, for instance, higher fatty acid glycerides [e.g., cacao butter, Witepsols (Dinamit-Nobel), etc.], medium-chain fatty acids [e.g., Migriols (Dinamit-Nobel), etc.], vegetable oils (e.g., sesame oil, soybean oil, cotton-seed oil, etc.), etc. The water-soluble base includes, for instance, polyethylene glycols propylene glycol, etc. The hydrophilic base includes, for instance, natural gums, cellulose derivatives, vinyl polymers, and acrylic polymers, etc.

Dosages

The dosage of the pharmaceutical composition of the present invention may be appropriately determined with reference to the dosages recommended for the respective active components and can be selected appropriately according to the recipient, the recipient's age and body weight, current clinical status, administration time, dosage form, method of administration, and combination of the active components, among other factors. For example, the dosage of the insulin sensitivity enhancer for an adult can be selected from the clinical oral dose range of 0.01 to 30 mg/kg body weight (preferably 0.05 to 10 mg/kg body weight, more preferably 0.05 to 5 mg/kg body weight) or the clinical parenteral dose range of 0.005 to 10 mg/kg body weight preferably 0.01 to 10 mg/kg body weight, more preferably 0.01 to 1 mg/kg body weight). The other active component or components having different modes of action for use in combination can also be used in dose ranges selected by referring to the respective recommended clinical dose ranges.

The proportions of the active components in the pharmaceutical composition of the present invention can be appropriately selected according to the recipient, the recipient's age and body weight, current clinical status, administration time, dosage form, method of administration, and combination of active components, among other factors.

Pharmaceutical Combinations

The present invention includes within its scope pharmaceutical compositions including, as an active ingredient, a therapeutically effective amount of at least one of the compounds of the invention, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

The pharmaceutical combinations of the present invention can be formulated in combination, or separately by mixing the respective active components either together or independently with a physiologically acceptable carrier, excipient, binder, diluent, etc. When the active components are formulated independently, the respective formulations can be extemporaneously admixed using a diluent or the like and administered or can be administered independently of each other, either concurrently or at staggered times to the same subject. So, such other therapeutic agent(s) may be administered prior to, simultaneously with, or following the administration of the melanin-concentrating hormone receptor (MCHR) antagonists in accordance with the invention.

Examples of suitable anti-obesity agents for use in combination with the compounds of the present invention include melanocortin receptor (MC4R) agonists, cannabinoid receptor modulators, growth hormone secretagogue receptor (GHSR) antagonists, galanin receptor modulators, orexin antagonists, CCK agonists, GLP-agonists, and other Pre-proglucagon-derived peptides; NPY1 or NPY5 antagonist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inhibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491, 134, 5,776,983 and 5,488,064, a thyroid receptor beta modulator, such as a thyroid receptor ligand as disclosed in WO 97/21993 (U. Cal SF), WO 99/00353 (KaroBio) and WO 00/039077 (KaroBio), a lipase inhibitor, such as orlistat or ATL-962 (Alizyme), serotonin receptor agonists, (e.g., BVT-933 (Biovitrum) or lorcaserin (Arena)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazinidol, anorectic agents such as topiramate (Johnson & Johnson), CNTF (ciliary neurotrophic factor)/AXOKNE® (Regeneron), BDNF (brain-derived neurotrophic factor), leptin and leptin receptor modulators, or cannabinoid-1 receptor inverse agonists/neutral antagonists, such as SR-141716 (Sanofi) or SLV-319 (Solvay) and DGAT inhibitors such as those described in WO 2006/134317 (A1) (Astra Zeneca), WO 2006/044775 (A2) (Bayer), WO 2006/06019020 (A1) (Sankyo), WO 2006/082010 (A1) (Roche), WO 2004/047755 (A2) (Japan Tobacco, Tularik), and WO 2005/0727401 (A2) (Amgen, Japan Tobacco).

Examples of suitable anti-diabetic agents for use in combination with the compounds of the present invention include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors including saxagliptin, vildagliptin and sitagliptin, SGLT2 inhibitors including dapagliflozin and serglifozin, glycogen phosphorylase inhibitors, and/or meglitinides, as well as insulin, and/or glucagon-like peptide-1 (GLP-1), GLP-1 agonist, SIRT activators (resveratrol) and/or a PTP-1B inhibitor (protein tyrosine phosphatase-1B inhibitor).

The antidiabetic agent may be an oral antihyperglycemic agent preferably a biguanide such as metformin or phenformin or salts thereof preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594,016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), N,N-2344 (Dr. Reddy/NN), or YM-440 (Yamanouchi), preferably rosiglitazone and pioglitazone.

The compounds of the present invention may be employed with a PPARα/γ dual agonist such as MK-767/KRP-297 (Merck/Kyorin; as described in Yajima, K. et al., *Am. J. Physiol. Endocrinol. Metab.*, 284:E966-E971 (2003)), AZ-242 (tesaglitazar; Astra-Zeneca; as described in Ljung, B. et al., *J. Lipid Res.*, 43:1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactonae derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al., *J. Med. Chem.*, 31:1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A. et al., *Curr. Pharm. Des.*, 2:1-40 (1996).

In addition, other squalene synthetase inhibitors suitable for use herein include the terpenoid pyrophosphates disclosed by Ortiz de Montellano, P. et al., *J. Med. Chem.*, 20:243-249 (1977), the farnesyl diphosphate analog A and presqualene pyrophosphate (PSQ-PP) analogs as disclosed by Corey et al., *J. Am. Chem. Soc.*, 98:1291-1293 (1976), phosphinylphosphonates reported by McClard, R. W. et al., *J. Am. Chem. Soc.*, 109:5544 (1987) and cyclopropanes reported by Capson, T. L., Ph.D., dissertation, Dept. Med. Chem., Univ. Utah, Abstract, Table of Contents, pp. 16, 17, 40-43, 48-51, Summary (June 1987).

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SEC-HOLEX®, Policexide) and cholestagel (Sankyo/Geltex), as well as LIPOSTABIL® (Rhone-Poulenc), EISAI® E-5050 (an N-substituted ethanolamine derivative), imanixil (HOE-402), tetrahydrolipstatin (THL), istigmastanylphos-phoryl-choline (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, Drugs of the Future, 24:9-15 (1999) (Avasimibe); Nicolosi et al., "The ACAT inhibitor, C1-1011 is effective in the prevention and regression of aortic fatty streak area in hamsters", Atherosclerosis (Shannon, Irel.), 137(1):77-85 (1998); Ghiselli, G., "The pharmacological profile of FCE 27677: a novel ACAT inhibitor with potent hypolipidemic activity mediated by selective suppression of the hepatic secretion of ApoB100-containing lipoprotein", Cardiovasc. Drug Rev., 16(1):16-30 (1998); Smith, C. et al., "RP 73163: a bioavailable alkylsulfinyl-diphenylimidazole ACAT inhibitor", Bioorg. Med. Chem. Lett., 6(1):47-50 (1996); Krause, B. R. et al., Chapter 6: "ACAT Inhibitors: Physiologic Mechanisms for Hypolipidemic and Anti-Atherosclerotic Activities in Experimental Animals", Inflammation: Mediators and Pathways, CRC Press, Inc., publ., Ruffolo, Jr., R. R. et al., eds., pp. 173-198 (1995); Sliskovic et al., "ACAT inhibitors: potential anti-atherosclerotic agents", Curr. Med. Chem., 1(3):204-225 (1994); Stout et al., "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", Chemtracts: Org. Chem., 8(6):359-362 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in Atherosclerosis, 115:45-63 (1995) and J. Med. Chem., 41:973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal Na$^+$/bile acid cotransporter inhibitor such as disclosed in Drugs of the Future, 24:425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 00/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SPEBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin, rosuvastatin, and ezetimibe as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and/or T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043, 265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

MCHR1 antagonists could be useful in treating other diseases associated with obesity, including sleep disorders. Therefore, the compounds described in accordance with the present invention could be used in combination with therapeutics for treating sleep disorders. Examples of suitable therapies for treatment of sleeping disorders for use in combination with the compounds of the present invention include melatonin analogs, melatonin receptor antagonists, ML 1 B agonists, GABA receptor modulators; NMDA receptor modulators, histamine-3 (H3) receptor modulators, dopamine agonists and orexin receptor modulators.

MCHR1 antagonists may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

MCHR1 antagonists may reduce anxiety or depression; therefore, the compounds described in accordance with the present invention may be used in combination with anti-anxiety agents or antidepressants. Examples of suitable anti-anxiety agents for use in combination with the compounds of the present invention include benzodiazepines (e.g., diazepam, lorazepam, oxazepaam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present invention include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpha-adrenoreceptor antagonists, and atypical antidepressants (bupropion, lithium, nefazodone, trazodone and viloxazine).

The combination of a conventional antipsychotic drug with a MCHR1 antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present invention include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), diphenylbutylpiperidine (pimozide) and indolone (molindolone) classes of antipsychotic agents. Other antipsychotic agents with potential therapeutic value in combination with the compounds in the present invention include loxapine, sulpiride and risperidone.

Combination of the compounds in the present invention with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, schizoaffective disorder, delusional disorder, brief psychotic disorder and psychotic disorder not specified. Examples of suitable antipsychotic drugs for combination with the compounds in the present invention include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

Methods of Preparation

As summarized in Scheme 1, compounds of the present invention represented by structures of Formulae 1A and 1B may be prepared in one step by condensing compounds of formula 2 with compounds of formula 3 in an organic solvent such as hot EtOH or preferably molten phenol to generate the compounds of the present invention.

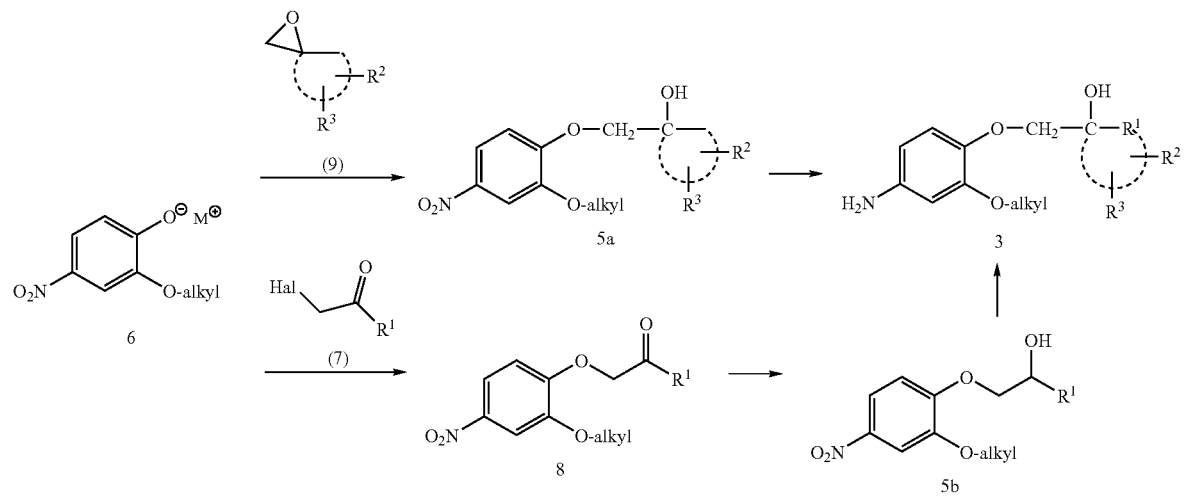

Scheme 1

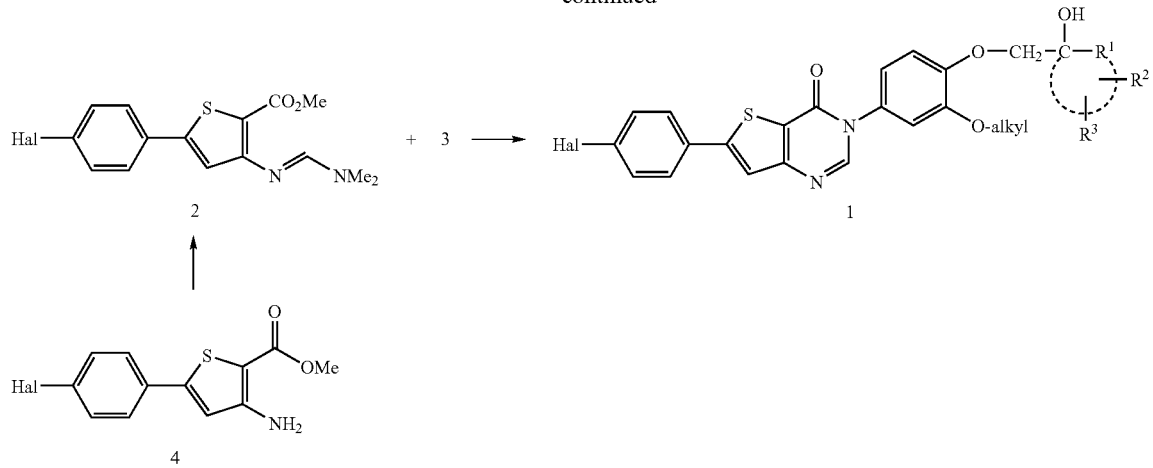

Compounds of formula 2 can be prepared as described in WO2003/033476, incorporated herein by reference in its entirety, by heating compounds of formula 4 with dimethylformamide dimethyl acetal.

Preparation of compounds of formula 4 is described in WO1998/49899 which is incorporated herein by reference in its entirety.

Anilines of formula 3 may be prepared by reduction of nitro aromatics of formula 5a or 5b either by catalytic hydrogenation using a catalyst such as Pd/C in a solvent such as EtOH, MeOH or in an ethyl acetate-alcohol co-solvents (Scheme 1).

Alternatively, compounds of formula 5b for which $R^1$ is a cycloalkyl ring and both the dotted lines and $R^2$ and $R^3$ are not present, can be prepared by enzymatic reduction of the ketone 8, for example, employing ketoreductases such as ketoreductase (KRED) 112 or ketoreductase (KRED) 113 (Biocatalytics, Inc.) or by microbial conversion of ketone 8 to produce alcohol 5b, for example, employing *Candida sonorensis* SC16117 (ATCC® #56511).

Alternatively, reduction of compounds of formula 5a or 5b with $SnCl_2$ in a solvent such EtOAc can be employed to generate anilines of formula 3.

Compounds of formula 5b, for which $R^1$ is a cycloalkyl ring and both the dotted lines and $R^2$ and $R^3$ are not present, can most easily be prepared from compounds of formula 6 by a sequential alkylation and reduction sequence entailing alkylation of 6 with an appropriate alkylating agent such as an α-haloketone as depicted by formula 7 in the presence of a base such as $Cs_2CO_3$ or $K_2CO_3$ in a solvent such as DMF followed by reduction of the intermediary ketone 8. The reduction can be achieved under either achiral conditions employing a reagent such as $NaBH_4$ in a solvent such as EtOH followed by resolution or alternatively under chiral conditions employing an enzyme or a chiral reagent by employing procedures readily known to those skilled in the art.

Alternatively compounds of formula 5a, for which $R^1$ is absent and the substituted carbocycle connoted by the dotted lines and $R^2$ and $R^3$ are present, can be directly prepared by heating the alkali metal salt (Na or K) of compounds of formula 6 with epoxides of formula 9 thermally or by microwave at temperatures ranging from 100-180° C. in a solvent such as 85% $MeCN/H_2O$ containing sufficient $NaH_2PO_4$ to buffer the pH as the reaction progresses.

Epoxides of formula 9 are either commercially available or readily prepared employing procedures readily known to those skilled in the art.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

Abbreviations

The following abbreviations are employed herein:
Ph=phenyl
Bn=benzyl
t-Bu=tertiary butyl
Me=methyl
Et=ethyl
TMS trimethylsilyl
TBS=tert-butyldimethylsilyl
THF=tetrahydrofuran
$Et_2O$=diethyl ether
EtOAc=ethyl acetate
DMF=dimethyl formamide
MeOH=methanol
EtOH=ethanol
i-PrOH=isopropanol
HOAc or AcOH=acetic acid
TFA=trifluoroacetic acid
i-$Pr_2$NEt=diisopropylethylamine
$Et_3$N=triethylainine
DMAP=4-dimethylaminopyridine
$NaBH_4$=sodium borohydride
n-BuLi=n-butyllithium
Pd/C=palladium on carbon
KOH=potassium hydroxide
NaOH=sodium hydroxide
LiOH=lithium hydroxide
$K_2CO_3$=potassium carbonate
$NaHCO_3$=sodium bicarbonate
Ar=argon
$N_2$=nitrogen min=minute(s)
h or hr=hour(s)
L=liter
mL=milliliter
µL microliter
g=gram(s)
mg=milligram(s)
mol=moles
mmol=millimole(s)
meq=milliequivalent
RT=room temperature
sat or sat'd=saturated
aq.=aqueous
TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp=melting point

EXAMPLES

The following Examples serve to better illustrate, but not limit, some of the preferred embodiments of the invention.

Where possible a modular convergent approach was utilized to prepare the following Examples entailing synthesis of the appropriate aniline, condensation with a formamide to generate the bioactive thienopyrimidone followed by subsequent elaboration to convert the alcohol moiety to a prodrug.

Example 1

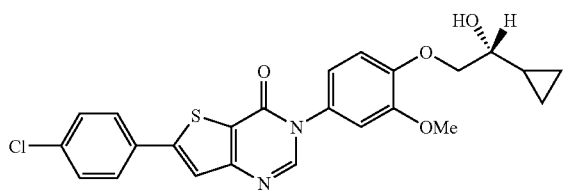

A. 2-Bromo-1-cyclopropylethanone

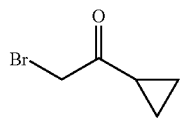

Following the procedure described by Calverley, M. J. et alt, *Tetrahedron Lett.*, 43:4609 (1987), Br$_2$ (21.72 mL, 422 mmol) was added over 5 min to a solution of 1-cyclopropylethanone (35.44 g, 421 mmol) in MeOH (250 mL) at 0° C. Decolorization occurred as the resulting dark orange solution was stirred at <10° C. for 50 min. After removal of the ice bath, the mixture was stirred at 20° C. for another 0.5 h; whereupon, 30 ml of water was added. After stirring an additional 15 min, the reaction was diluted with 90 ml water prior to extraction with 200 mL of Et$_2$O (4×). The combined organic layers were sequentially washed with 1M Na$_2$CO$_3$ (150 ml) and brine (100 ml) before drying over any. MgSO$_4$. After filtration and concentration using a rotary evaporator, the crude product was obtained as colorless oil. Subsequent distillation at 13 mm Hg yielded 40.9 g of 2-bromo-1-cyclopropylethanone as a colorless oil bp 58-62° C. $^1$H NMR (500 MHz, CDCl$_3$) δ ppm 0.95-1.03 (m, 2H), 1.08-1.15 (m, 2H), 2.13-2.21 (m, 1H), 4.00 (s, 2H).

B. 1-Cyclopropyl-2-(2-methoxy-4-nitrophenoxy)ethanone

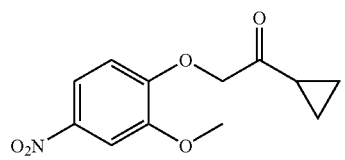

An orange suspension of 4-nitroguaiacol potassium salt hydrate (31.7 g, 153 mmol) and 2-bromo-1-cyclopropylethanone (29.4 g, 180 mmol), prepared in part A, in DMF (310 mL) was heated at 80° C. for 1 h. LC-MS analysis revealed the conversion to product was complete. The resulting yellow reaction mixture was diluted with water (932 ml) and stirred for 4 hr as the mixture cooled to 20° C. Subsequent filtration yielded a yellow filter cake which after washing 3× with 150 mL of H$_2$O and air drying yielded 34.6 g of 1-cyclopropyl-2-(2-methoxy-4-nitrophenoxy)ethanone as a light yellow solid. M.P. 112-113° C. $^1$H NMR (400 MHz, CDCl$_3$): δ ppm 0.95-1.03 (m, 2H), 1.13-1.18 (m, 2H), 2.15-2.23 (m, 1H), 3.95 (s, 3H), 4.86 (s, 2H), 6.73 (d, J=8.7 Hz, 1H), 7.75 (d, J=2.7 Hz, 1H), 7.82 (dd, J=8.7, 2.7 Hz, 1H). $^{13}$C NMR (100 MHz, CDCl$_3$) δ ppm 205.2, 152.7, 149.1, 117.3, 111.6, 106.9, 73.5, 56.3, 17.1, 12.0. HPLC: 5.8 min retention time, 98.7% API; ZORBAX® column SB C018 4.6×75 mm; flow rate 2.5 ml/min; Gradient solvent system: from 10% A:0% B to 0% A:110% B for 8 min (Solvent A: 10% MeOH–90% H$_2$O=0.2% H$_3$PO$_4$; Solvent B: 90% MeOH–10% H$_2$O+0.2% H$_3$PO$_4$) Detection at 220 nm. LC/MS: m/e 252.3 (M+H); 4 min gradient; 2.35 min retention.

C. (R)-1-Cyclopropyl-2-(2-methoxy-4-nitrophenoxy)ethanol (Part C(R)-Alcohol)

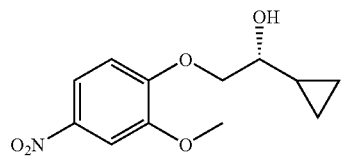

C. Preparation (1)

To a yellow suspension of 1-cyclopropyl-2-(2-methoxy-4-nitrophenoxy)ethanone (34.6 g, 138 mmol), prepared in Part B, in EtOH (356 mL) at 0° C. was added NaBH$_4$ (3.1 g, 82 mmol) over 15 min. After removal of the ice bath, the temperature was not allowed to exceed 20° C. while the reaction stirred for 35 additional min. During this period the color progressively became a deeper yellow hue. The stirred reaction was cooled to ~10° C. using an ice bath prior to cautious slow addition of HOAc (12 mL, 210 mmol) to minimize the rate of evolution of $H_2$ gas. After stirring for 0.5 h following cessation of gas evolution, the yellow suspension was concentrated under vacuum using a rotary evaporator to remove ~300 mL of EtOH. Filtration yielded a light yellow solid (28.7 g) after washing with $H_2O$ and air drying. Subsequent further concentration of the filtrate to remove most of the EtOH resulted in more precipitate forming which, after filtration as described previously, corresponded to an additional 4.9 g of desired product. The two fractions were combined to yield 33.6 g of racemic 1-cyclopropyl-2-(2-methoxy-4-nitrophenoxy)ethanol.

Racemic 1-cyclopropyl-2-(2-methoxy-4-nitrophenoxy)ethanol (45.1 g, mmol) in 2/1 MeCN/1-PrOH (451 mL) was resolved by chiral chromatography resolution using a CHIRALPAK® AD-H (3×25 cm, 5 μm) column under the Chiral-SFC conditions. The chromatographic conditions employed an 85/15 mixture of $CO_2$/i-PrOH as the mobile solvent with a flow rate of 130 mL/min at 35° C. with the BPR pressure maintained at 100 bar and detector wavelength at 234 nM. Each 0.7 mL injection required a run time of 7 min. The chiral purity of the R enantiomer was determined to be greater than 99.9% at 234 nm based on SFC/UV area % using analytical SFC conditions. Concentration of the resultant eluant under vacuum using a rotary evaporator yielded (R)-1-cyclopropyl-2-(2-methoxy-4-nitrophenoxy)ethanol as yellow oil. Subsequent dissolution in 150 ml EtOH and reconcentration yielded the title compound in the form of a yellow oil which solidified to form a light yellow solid (20.9 g) upon drying under high vacuum overnight. M.P. 77° C. $^1H$ NMR (400 MHz, $CDCl_3$): δ ppm 0.30-0.37 (m, 1H), 0.42-0.50 (m, 1H), 0.55-0.69 (m, 2H), 0.97-1.08 (m, 1H), 2.40-2.70 (bs, 1H), 3.41 (ddd, J=8.3, 8.3, 2.7 Hz, 1H), 3.93 (s, 3H), 4.10 (dd, J=9.3, 8.0 Hz, 1H), 4.23 (dd, J=9.3, 2.7 Hz, 1H), 6.95 (d, J=8.8 Hz, 1H), 7.74 (d, J=2.2 Hz, 1H), 7.89 (dd, J=8.8, 2.2 Hz, 1H). $^{13}C$ NMR (100 MHz, $CDCl_3$) ppm 153.7, 149.2, 141.7, 117.6, 111.5, 106.7, 74.4, 73.5, 56.2, 13.4, 2.7, 2.0. HPLC: 6.26 min retention time, 98.7% API; ZORBAX® column SB C18 4.6×75 mm; flow rate 2.5 ml/min; Gradient solvent system: from 100% A:0% B to 0% A:100% B for 8 min (Solvent A: 10% MeOH–90% $H_2O$=0.2% $H_3PO_4$; Solvent B: 90% MeOH–10% $H_2O$+0.2% $H_3PO_4$) Detection at 220 nm. LC/MS: m/e=254.3 (M+H).

Chiral HPLC: Optical purity was assessed by HPLC chromatography at 35° C. using a CHIRALPAK® AD-H, 25×4.6 mm ID; 5 μm column for which the mobile phase was a 80/20 mixture of $CO^2$/isopropanol % isopropanol at 100 bars with a flow rate of 2 mL/min. Under these conditions the desired R enantiomer eluted in 7 minutes followed by the S enantiomer at 8.5 min.

C. Preparation (2)

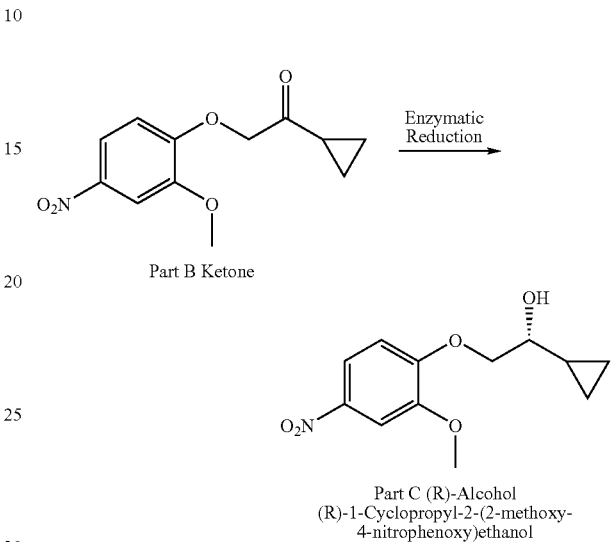

Part B Ketone

Part C (R)-Alcohol
(R)-1-Cyclopropyl-2-(2-methoxy-4-nitrophenoxy)ethanol

Two commercially available ketoreductases from Biocatalytics, Inc., namely KRED-112 and KRED-113, were employed for the reduction of Part B ketone to corresponding Part C(R)-alcohol. The reactions were carried out at 30° C. in 100 mM phosphate buffer, pH47.5 with substrate input of 4-10 mg/mL and enzyme input of 2-5 mg/mL. Isopropaniol and NADP were used to regenerate cofactor NADPH required for the reduction process. Glucose dehydrogenase, NADP and glucose were also used to regenerate cofactor NADPH required for this reduction. Both reversed phase and chiral HPLC methods were established for determination of substrate and product concentrations and the enantiomeric excess of product.

Two ketoreductases, KRED 112 and KRED 113, gave 97-99% yields and 99.5% enantiomeric excess for the desired Part C(R)-alcohol. Results are as shown in the table below:

| | Reduction of Part B Ketone to Part C (R)-Alcohol (IPA-200 μL, pH 7.5, 30° C.) | | | | | |
|---|---|---|---|---|---|---|
| | Part B Ketone in DMSO | Enzyme Solution | | % Conversion (% ee of Part C (R)-alcohol) | | |
| Entry | (0.2 mg/μL) | (20 mg/mL) | Buffer | 24 h | 48 h | 66 h |
| KRED-113 | 4 mg/20 μL | 2 mg/100 μL | 700 μL | 95.8 | 99.1 (ee 99.6%) | 99.7 (ee 99.6%) |
| KRED-113 | 10 mg/50 μL | 5 mg/250 μL | 550 μL | 69.3 | 88.4 (ee 99.4%) | 97.4 (ee 99.5%) |
| KRED-112 | 4 mg/20 μL | 2 mg/100 μL | 750 μL | 68 | 84 (99.4%) | 97% (ee 99.6%) |

Employing the above procedure, two ketoreductases from Julich Enzyme Inc., namely ADH kit part 5/9 and ADH kit part 6/9, gave 44-48% yields and 100% enantiomeric excess for the (S)-alcohol.

HPLC Method

Reversed phase Chiral HPLC for determination of enantiomeric excess:
Column: CHIRALPAK® IC 5 μm, 250×4.6 mm
Solvent: Gradient of solvent A and B
A: 0.05% TFA in Water—Methanol (80:20)
B: 0.05% TFA in Acetonitrile—Methanol (80:20)
Start 30% B, 25 min 55% B, 30 min 100% B, 40 min 100% B
Total Time 40 min, Flow Rate: 0.5 ml/min, Room Temperature
UV detection 240 and 340 nm. 02.22

The retention times are:
(S)-Alcohol Retention time: 26.74 min
(R)-Alcohol Retention time: 24.9 min
Part B Ketone peak at 32.74 min C. Preparation (3)

Selective Enzymatic Reduction Process

Use of *Candida sonoresis* (SC 16117) for the Reduction of Part B Ketone: *Candida sonoresis* (SC 16117) (ATCC® #56511) was used for the reduction of Part B ketone to the corresponding Part C(R)-alcohol. Cultures were grown for 48 hours at 28° C. on a medium containing 2% glucose, 2% malt extract, 1% yeast extract, and 0.5% peptone. Cells were harvested by centrifugation and cells were suspended in 50 mM potassium phosphate buffer, pH 7.0 at 10% (w/v) cell concentrations. Cells were supplemented with 5 mg/mL of substrate, 50 mg/mL glucose, 5 mg/mL NADP and 5 units glucose dehydrogenase to regenerate NADPH required for this reduction. Reactions were carried out at 28° C. for 24 hours. Product concentrations aid enantiomeric excess of product was determined by HPLC.

*Candida sonorensis* SC 16117 (ATCC® #56511) produced the desired (R)-alcohol in 67% yield with 97% enantiomeric excess. Ketoreductase enzyme from *Candida sonorensis* SC16117 was purified to homogeneity from cell extracts. The purified protein reduced Part B ketone to corresponding Part C (R)-alcohol with 100% enantiomeric excess. Glucose, glucose dehydrogenase and NADP were used to regenerate cofactor NADPH required for reduction process.

D. (R)-2-(4-Amino-2-methoxyphenoxy)-1-cyclopropylmethanol

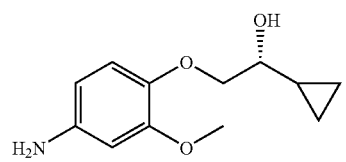

To a solution of (R)-1-cyclopropyl-2-(2-methoxy-4-nitrophenoxy)ethanol (20.90 g, 83 mmol), prepared in Part C, in EtOH (546 ml) was added 5% Pd/C, dry basis, Degussa type 50% water content (3.0 g, 0.705 mmol). The suspension was hydrogenated (1 atm. H$_2$, balloon) at 20° C. for 2.5 h; whereupon, LC/MS analysis revealed the reaction to be complete. After filtration of the reaction mixture through CELITE® pad and subsequent washing of the cake with EtOH, the filtrate was concentrated under vacuum using a rotary evaporator to yield (R)-2-(4-amino-2-methoxyphenoxy)-1-cyclopropylethanol as a brown solid. M.P. 71° C. (18.34 g, 100%). $^1$H NMR (400 MHz, CDCl$_3$): δ ppm 0.18-0.27 (m, 1H), 0.38-0.43 (m, 1H), 0.45-0.61 (m, 2H), 0.82-0.92 (m, 1H), 3.21 (ddd, J=8.8, 8.8, 2.6 Hz, 1H), 3.80 (s, 3H), 3.86 (dd, J=10.1, 8.8 Hz, 1H), 4.09 (dd, J=10.1, 2.6 Hz, 1H), 6.21 (dd, J=8.3, 2.7 Hz, 1H). 6.29 (d, J=2.7 Hz, 1H), 6.78 (d, J=8.3 Hz, 1H). $^{13}$C NMR (100 MHz, CDCl$_3$) δ ppm 151.2, 142.1, 140.8, 118.7, 106.9, 100.5, 76.5, 74.4, 55.7, 12.9, 2.5, 1.6. HPLC: 6.28 min retention time, 98.5% API; ZORBAX® column SB C18 4.6×75 mm; flow rate 2.5 ml/min; Gradient solvent system: from 100% A:0% B to 0% A:100% B for 8 min (Solvent A: 10% MeOH–90% H$_2$O=0.2% H$_3$PO$_4$; Solvent B: 90% MeOH–10% H$_2$O+0.2% H$_3$PO$_4$) Detection at 220 nm. LC/MS: m/e 224.5 (M+H); 4 min gradient.

E. (E)-Methyl 5-(4-chlorophenyl)-3-(2-(dimethylamino)vinyl thiophene-2-carboxylate

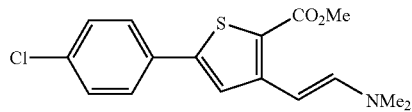

To a mixture of commercially available methyl 3-amino-5-(4-chlorophenyl)thiophene-2-carboxylate (75 g, 279 mmol) in EtOH (450 mL) was added 1,1-dimethoxy-N,N-dimethylmethanamine (56 mL, 420 mmol). The stirred reaction mixture was heated to reflux; whereupon within 30 min, the suspension became a clear solution. LC/MS analysis revealed that the reaction was complete after 4 hr. The mixture was cooled to room temperature and then concentrated under vacuum using a rotary evaporator to obtain a yellow-green oil. After addition of Et$_2$O (100 mL), the mixture was stirred as seed crystals were added. Continuation of stirring resulted in a rapid formation of a precipitate which was collected by filtration. After drying overnight under vacuum, 74.9 g of a light yellow solid was obtained. Concentration of the filtrate yielded another 4.5 g resulting in a combined yield of 79.4 g (88%) of methyl 5-(4-chlorophenyl)-3-(2-(dimethylamino)vinyl)thiophene-2-carboxylate. $^1$H NMR (400 MHz, CDCl$_3$): δ ppm 3.06 (s, 3H), 3.08 (s, 3H), 3.81 (s, 3H), 6.98 (s, 1H), 7.33-7.38 (m, 2H), 7.51-7.56 (m, 2H), 7.68 (s, 1H). $^{13}$C NMR (100 MHz, CDCl$_3$) δ ppm 163.2, 159.1, 156.0, 145.7, 134.4, 132.2, 129.1, 126.9, 122.3, 112.4, 51.4, 40.2, 34.3. HPLC: 6.14 min retention time, 85.1% API; ZORBAX® column SB C18 4.6×75 mm; flow rate 2.5 ml/min; Gradient solvent system: from 100% A:0% B3 to 0% A:100% B for 8 min (Solvent A: 10% MeOH–90% H$_2$O=0.2% H$_3$PO$_4$; Solvent B: 90% MeOH–10% H$_2$O+0.2% H$_3$PO$_4$) Detection at 220 nm. LC/MS: m/e 323.3 (M+H); 4 min gradient.

F. (R)-6-(4-Chlorophenyl)-3-(4-(2-cyclopropyl-2-hydroxyethoxy)-3-methoxyphenyl)-thieno[3,2-d]pyrimidin-4(3H)-one

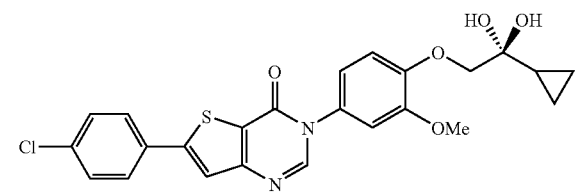

A mixture of methyl 5-(4-chlorophenyl)-3-((dimethylamino)methyleneamino)thiophene-2-carboxylate (85 g, 263 mmol), prepared in Part E, the aniline prepared in Part D (52 g, 233 mmol) and phenol (230 g, 2444 mmol) was heated at 130° C. for 30 min. The resulting black sticky syrup was cooled to room temperature prior to dilution with Et$_2$O (300 mL). The resulting mixture was stirred at room temperature for 20 min and then filtered. After washing the filter cake with Et$_2$O (600 mL), HPLC analysis indicated that the product contained 6% phenol. In addition, some product remained in the black filtrate. Dissolution of the filter cake in CH$_2$Cl$_2$ (200 mL) generated an orange solution which, upon being stirred after dilution with Et$_2$O (400 mL), generated a precipitate. The resulting solid was collected by filtration and dried in an oven at 40° C. to give the desired title compound as an off-white solid (81 g, 74.2% yield). MP 178-179° C. $^1$H NMR (400 MHz, DMSO-d$_6$) δ ppm 0.29-0.45 (m, 4 H), 0.91-1.01 (ml, 1 H), 3.34-3.39 (m, 1 H), 3.79 (s, 3 H), 3.96-4.05 (m, 2 H), 7.04 (dd, 1 H), 7.13 (d, J=8.2 Hz, 1 H), 7.19 (s, 1 H), 7.58 (d, J=8.8 Hz, 2 H), 7.92 (d, J=8.2 Hz, 2 H), 7.97 (s, 1 H), 8.40 (s, 1 H). $^{13}$C NMR (100 MHz, DMSO-d$_6$) δ ppm 1.33, 1.66, 14.11, 55.79, 71.16, 73.18, 111.86, 112.81, 119.61, 121.71, 122.04, 127.84, 129.27, 129.68, 131.22, 134.27, 148.61, 148.99, 149.48, 149.78, 156.09, 157.40. HPLC: 8.29 min retention time, >99% API; ZORBAX® column SB C18 4.6× 75 mm; flow rate 2.5 ml/min; Gradient solvent system: from 100% A:0% B to 0% A: 100% B for 8 min (Solvent A: 10% MeOH–90% H$_2$O=0.2% H$_3$PO$_4$; Solvent B: 90% MeOH– 10% H$_2$O+0.2% H$_3$PO$_4$) Detection at 220 nm. LC/MS: m/e 469.3 (M+H); 4 min gradient.

Chiral HPLC: Optical purity was assessed by HPLC chromatography at 25° C. using a CHIRALCEL® OD, 250×4.6 mm ID; 10 μm column for which the mobile phase was 60% isopropanol with 40% heptane with a flow rate of 3 mL/min. Under these conditions the desired R enanatiomer eluted in 13.2 minutes followed by the S enantiomer at 19.7 min.

Example 2

6-(4-Chlorophenyl)-3-(4-((3,3-difluoro-1-hydroxycyclobutyl)methoxy)-3-methoxyphenyl)thieno[3,2-d]pyrimidin-4(3H)-one

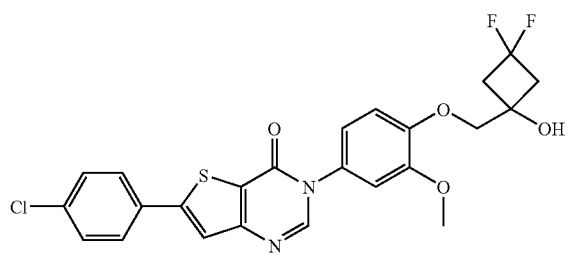

A. 3,3-Difluoro-N,N-dimethylcyclobutanecarboxamide

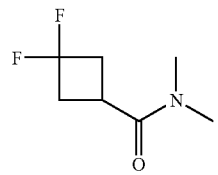

Oxalyl chloride (21.74 mL, 248 mmol) was added dropwise to a stirred solution of 3,3-difluorocyclobutanecarboxylic acid (26 g, 191 mmol; prepared as described in ref: Elend, D. et al., *Syn. Comm.*, 35:657 (2005)) in CH$_2$Cl$_2$ (500 mL) and DMF (0.5 mL) at 0° C. The reaction mixture was allowed to come to RT and stirred at RT for 1h prior to being concentrated at RT using a rotary evaporator at ca. 50 mm Hg vacuum. After adding THF (300 μL) to the resulting residue, the stirred solution was cooled 0° C. prior to addition of a 2M solution of Me$_2$NH (478 mL, 955 mmol) in THF. After stirring the reaction mixture at RT for 0.5 h, the mixture was partitioned between ether and 5% aq. Na$_2$CO$_3$. The organic layer was dried over MgSO$_4$ and concentrated in vacuo at RT. After portioning the residue between CH$_2$Cl$_2$ and water, the organic layer was dried over MgSO$_4$ and concentrated in vacuo at RT to give 3,3-difluoro-N,N-dimethylcyclobutanecarboxamide (24 g, 147 mmol, 77% yield) as a brown semi solid, used as such in the next step, $^1$H NMR (400 MHz, CDCl$_3$) δ ppm 2.82-3.13 (9 H, m), 2.62-2.79 (2 H, m).

B. 1-(3,3-Difluorocyclobutyl)-N,N-dimethylmethanamine

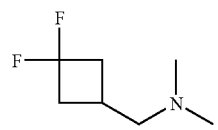

A solution of 3,3-difluoro-N,N-dimethylcyclobutanecarboxamide (24 g, 147 mmol) prepared in Part A in THF (500 mL) was added to a stirred suspension of lithium aluminum hydride (7.5 g, 198 mmol) in 500 in THF at 0° C. The mixture was allowed to come to RT. After stirring the reaction mixture at RT for 18 h, it was quenched by slowly adding 10 mL 6 N NaOH and 5 mL water at 5° C. with stirring. The mixture was stirred at RT for 0.5 h, dried over Na$_2$SO$_4$ and filtered. The filtrate was concentrated to ca. 30 mL by a careful distillation of most of the THF using a vigreux column. The remaining material was distilled under slightly reduced pressure (ca. 100-200 mm Hg); the fraction (20 mL, bp 70-90° C.) contained the title compound contaminated with THF. The residual THF was carefully purged with a gentle stream of nitrogen to yield 1-(3,3-difluorocyclobutyl)-N,N-dimethylmethanamine (12 g, 80 mmol, 54.7% yield). $^1$H NMR (400 MHz, CDCl$_3$) δ ppm 2.46-2.94 (2 H, m), 2.38 (2 H, d, J=6.55 Hz), 2.16-2.28 (9 H, m).

C. 1-(3,3-Difluorocyclobutyl)-N,N-dimethylmethanamine oxide hydrate

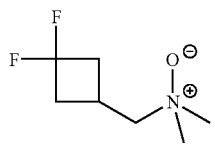

Ref. Cope, A. C. et al., *Org. Syn. Coll.*, IV:612-615; Doering et al., *J. Am. Chem. Soc.*, 89(17):4534 (1967).

30% Aqueous $H_2O_2$ (18 mL) was added dropwise to a stirred solution of 1-(3,3-difluorocyclobutyl)-N,N-dimethylmethanamine (12 g, 80 mmol) prepared in Part B in methanol (100 mL) at 5 to 22° C. over 2 h. After stirring at RT for 20 h, additional 30% $H_2O_2$ (18 mL) was added. After 3 h, Pd black slurry (150 mg) in water (3 mL) was added to the stirred reaction mixture in small portions such that the temperature could be maintained between 5 to 25° C. with a cooling bath. The reaction mixture was stirred at RT for 1 h until the $O_2$ evolution ceased. After filtration, the filtrate was concentrated in vacuo to give 1-(3,3-difluorocyclobutyl)-N,N-dimethylmethanamine oxide hydrate as a thick colorless oil (15 g, semisolid). $^1$H NMR (400 MHz, $CD_3OD$) δ ppm 3.47 (2 H, d, J=5.29 Hz), 3.16 (6 H, s), 2.75-2.92 (3 H, m), 2.42-2.58 (2 H, m).

D. 1,1-Difluoro-3-methylenecyclobutane

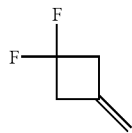

In order to remove most of the water from the sample, 1-(3,3-difluorocyclobutyl)-N,N-dimethylmethanamine oxide hydrate (15 g, 91 mmol) prepared in Part C was heated under vacuum (10 mm) at 100° C. using a distillation setup with the receiving flask cooled to −78° C. Once the water had been removed, the temperature was gradually increased to 165° C. After ca. 1 h most of the starting material had been pyrolyzed (a small amount of dark brown material remained in the distillation flask). Contents of the receiving flask were then washed sequentially with 5% aq. HCl (3×3 mL) and sat. $NaHCO_3$ (5 mL). The organic layer (olefin) was filtered through $Na_2SO_4$ giving 1,1-difluoro-3-methylenecyclobutane (5.5 g, 52.8 mmol, 58.2% yield) as a colorless oil. $^1$H NMR (400 MHz, $CDCl_3$) δ ppm 5.10 (2 H, quin, J=2.52 Hz), 2.77-3.57 (4 H, m).

E. 5,5-Difluoro-1-oxaspiro[2.3]hexane

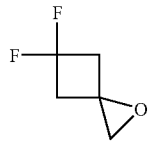

Meta chloroperbenzoic acid (74.6 g, 303 mmol) was added in small portions to a stirred solution of 1,1-difluoro-3-methylenecyclobutane (21.0 g, 202 mmol) prepared in Part U in $CH_2Cl_2$ (600 mL) at RT. The reaction mixture cooled with a water bath during the addition. After ca. 1 h the onset of a slight exotherm prompted further cooling using ice-water mixture. The reaction mixture was allowed to come to RT over 3 h. After stirring at RT for 16 h, additional m-CPBA (10 g) was added. The reaction mixture was stirred at RT for 24 h prior to being stored overnight in a refrigerator at 4° C. to precipitate out some of the acids. After filtration, the filtrate was washed with 10% $Na_2CO_3$. The organic layer was dried ($Na_2SO_4$), concentrated to ca. 170 mL using a Vigreux column. This material was flash distilled at ca. 10 mm to −78° C. traps (two traps in series were employed to minimize loss). The distillate was concentrated using a vigreux column to a volume of approximately 50 mL affording a 3:1 mixture of $CH_2Cl_2$:5,5-difluoro-1-oxaspiro[2.3]hexane (80 g, 200 mmol, 99% yield) by NMR. This material was used without further purification in the next step. $^1$H NMR (400 MHz, $CDCl_3$) δ ppm 2.91-3.16 (4 H, m), 2.88 (2 H, s).

F. 3,3-Difluoro-1-((2-methoxy-4-nitrophenoxy)methyl)cyclobutanol

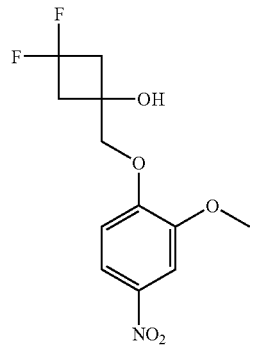

A mixture of 5,5-difluoro-1-oxaspiro[2.3]hexane+3 eq. $CH_2Cl_2$ (22.52 g, 0.06 mol), potassium 2-methoxy-4-nitrophenolate (12.43 g, 0.060 mol) prepared in Part E and $NaH_2PO_4 \cdot H_2O$ (7.45 g, 0.054 mol) in 50 mL MeCN-water (85:15) was heated at 130° C. in a steel bomb for 3.5 h. The reaction mixture was diluted with EtOAc, washed with 5% $Na_2CO_3$, dried ($MgSO_4$) and concentrated. The crude product was recrystallized from ca. 150 mL MTBE giving 3,3-difluoro-1-((2-methoxy-4-nitrophenoxy)methyl)cyclobutanol (11.2 g, 0.039 mol, 64.5% yield) as a light yellow solid. An additional 1.2 g of a slightly less pure desired product was obtained upon concentration of the mother liquor to ca. 50 mL. $^1$H NMR (400 MHz, $CDCl_3$) δ ppm 7.89 (1 H, dd, J=8.94, 2.64 Hz), 7.76 (1 H, d, J=2.77 Hz), 6.95 (1 H, d, S=9.06 Hz), 4.16 (2 H, s), 3.94 (3 H, s), 3.36 (1 H, s), 2.73-2.92 (4 H, m).

G. 1-((4-Amino-2-methoxyphenoxy)methyl)-3,3-difluorocyclobutanol

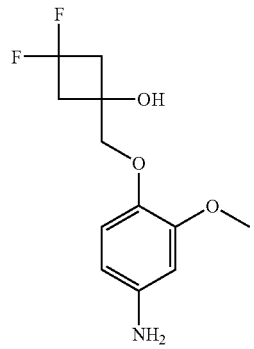

A mixture of 3,3-difluoro-1-((2-methoxy-4-nitrophenoxy)methyl)cyclobutanol (32.0 g, 111 mmol) prepared in Part F and 110% Pd/C (2.0 g, 1.879 mmol) in 700 mL MeOH was stirred under $H_2$ at 50 psi for 1.5 h. After filtration, the filtrate was concentrated to give 1-((4-amino-2-methoxyphenoxy)methyl)-3,3-difluorocyclobutanol (28.9 g, 111 mmol, quantitative yield) as a light purple solid. $^1$H NMR (400 MHz, $CD_3OD$) δ ppm 6.68 (1H, d, J=8.56 Hz), 6.35 (1 H, d, J=2.52 Hz), 6.16 (1 H, dd, J=8.31, 2.52 Hz), 4.77 (3 H, br. s.), 3.78 (2 H, s), 3.68 (3 H, s), 2.68-2.82 (2 H, m), 2.38-2.56 (2 H, m).

H. 6-(4-Chlorophenyl)-3-(4-((3,3-difluoro-1-hydroxycyclobutyl)methoxy)-3-methoxyphenyl)thieno[3,2-d]pyrimidin-4(3H)-one

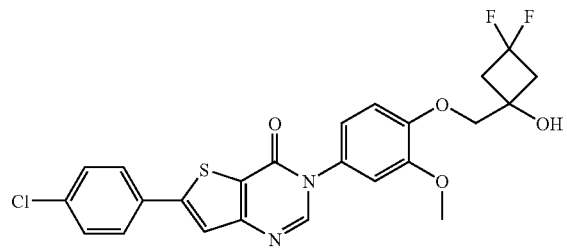

A stirred mixture of (E)-methyl 5-(4-chlorophenyl)-3-((dimethylamino)methylene-amino)thiophene-2-carboxylate (33.9 g, 105 mmol) prepared in Example 1 Part E and 1-((4-amino-2-methoxy-phenoxy)methyl)-3,3-difluorocyclobutanol (27.2 g, 105 mmol) prepared in Part C and phenol (200 g) was heated at 135-140° C. for 45 min while the reaction being monitored by LC. The mixture was diluted with methanol (700 mL), stirred at RT for 15 min and allowed to stand at RT overnight. The precipitated product was isolated by filtration, washed with chilled methanol and dried under vacuum to yield 6-(4-chlorophenyl)-3-(4-((3,3-difluoro-1-hydroxycyclobutyl)methoxy)-3-methoxyphenyl)thieno[3,2-d]pyrimidin-4(3H)-one (37 g, 73.3 mmol, 69.8% yield) as a white solid. Dilution of the mother liquor with $Et_2O$ and hexane precipitated more solid which was triturated with MeOH to yield 1.8 g of a second crop of the desired product. MP 198-199° C. $^1$H NMR (400 MHz, $CDCl_3$) δ ppm 8.14 (1 H, s), 7.66 (2 H, d, J=8.56 Hz), 7.54 (1 H, s), 7.45 (2 H, d, J=8.56 Hz), 7.08 (1 H, d, J=8.56 Hz), 6.99 (1 H, d, J=2.27 Hz), 6.95 (1 H, dd, J=8.31, 2.27 Hz), 4.14 (2 H, s), 3.89 (3 H, s), 2.72-2.93 (4 H, m). $^{13}$C NMR (126 MHz, $CDCl_3$) δ ppm 157.3, 156.7, 151.8, 150.4, 148.60 (1C, s), 148.0, 135.7, 131.4, 131.4, 129.4, 127.6, 123.1, 120.8, 119.4, 115.7, 117.6 (dd, J=282, 269. Hz), 111.4, 75.5, 64.6 (dd, J=18, 8 Hz), 56.0, 46.0 (t, J=22.89 Hz).

Examples 3 to 11

Prodrugs of the Examples 1 and 2 compounds were prepared to improve solubility and exposure. Standard conditions were employed to generate amino acid esters of both alcohols. Preparation of the respective half-esters of dibasic acids such as oxalic, malonic, succinic and glutaric acids are exemplified in Examples 7 and 11. Examples 3 and 8 exemplify preparation of a mono-phosphate ester.

Example 3

(R)-2-(4-(6-(4-Chlorophenyl)-4-oxothieno[3,2-d]pyrimidin-3(4H)-yl)-2-methoxyphenoxy)-1-cyclopropylethyl dihydrogen phosphate

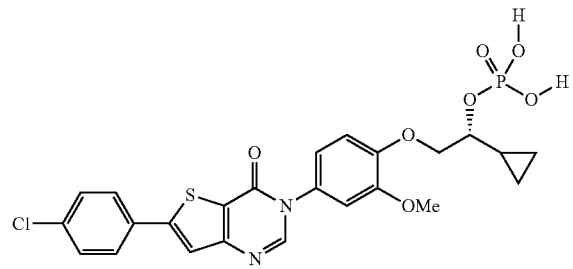

A. Bis(2-(trimethylsilyl)ethyl) diisopropylphosphoramidite

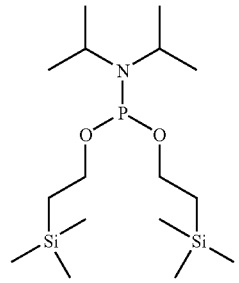

A solution of diisopropylphosphoramidous dichloride (10.8 g 50.78 mmoles) in $Et_2O$ (53 mL) in 250 mL three neck flask equipped with a temperature probe and addition funnel was cooled to 0 to −2° C. under $N_2$. A solution of 2-(trimethylsilyl)ethanol (12.6 g; 106.55 mmoles) and $Et_3N$ (15.4 g; 152.19 mmoles) in $Et_2O$ (84 mL) was added dropwise over 27-28 minutes to the stirred diisopropyl-phosphoramidous dichloride solution. A mild exotherm (+1-2° C.) accompanied the formation of a thick white suspension. After stirring overnight at 20° C., the mixture was filtered. The resultant cake was washed twice with 30 mL each of $Et_2O$. The combined filtrates were washed 2×100 mL of saturated aqueous $NaHCO_3$ followed by 40 mL of brine. After drying over $MgSO_4$ and concentrating to dryness under vacuum at room temperature, bis(2-(trimethylsilyl)ethyl) diisopropylphosphoramidite (18.12 g; 49.56 mmoles; 97.60% yield) was obtained as a clear colorless liquid. $^1$H NMR δ (400 MHz, $CDCl_3$): 3.90-3.78 (m, 4H), 3.77-3.68 (m, 2H), 1.31 (d, J=6.6 Hz, 12H), 1.17-1.12 (m, 4H), 0.15 (s, 18H). $^{13}$C NMR δ (100 MHz, $CDCl_3$): δ0.7 (2, d, $J_{C-P}$=19.1 Hz, 2C), 42.7 (1, d, $J_{C-P}$=12.7 Hz, 2C), 24.6 (3, d, $J_{C-P}$=7.6 Hz, 4C), 20.1 (2, d, $J_{C-P}$=7.6 Hz, 2C), −1.4 (3, 6C). $^{31}$P NMR δ (162 MHz, $CDCl_3$): 143.5 (s). LC/MS: m/e (M+H); 4 ml gradient; min retention.

B. (R)-2-(4-(6-(4-Chlorophenyl)-4-oxothieno[3,2-d]pyrimidin-3(4H)-yl)-2-methoxyphenoxy)-1-cyclopropylethyl bis(2-(trimethylsilyl)ethyl) phosphate

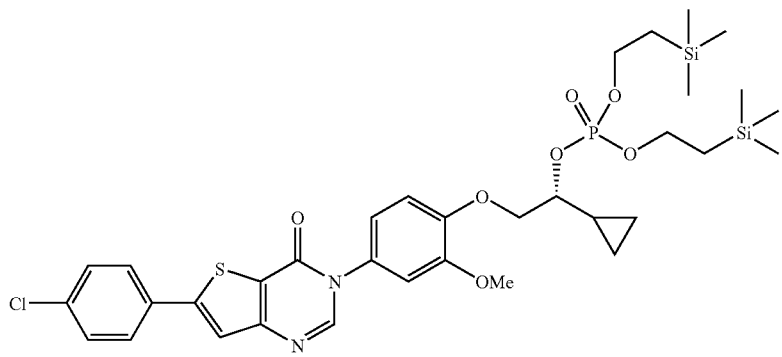

To a 250 mL 3 neck round bottom flask equipped with reflux condenser and temperature probe and flushed with $N_2$, was added (R)-6-(4-chlorophenyl)-3-(4-(2-cyclopropyl-2-hydroxyethoxy)-3-methoxyphenyl)-thieno[3,2-d]pyrimidin-4(3H)-one (6.33 g; 13.50 mmoles) (prepared in Example 1), 1H-1,2,4-triazole (1.89 g; 27.02 mmoles), and anhydrous $CH_2Cl_2$ (65 mL) at 20° C. To the resulting thick white suspension was added bis(2-(trimethylsilyl)ethyl) diisopropylphosphoramidite (9.8 g; 26.80 mmoles), prepared in Part A. The stirred reaction was heated to reflux (40° C. internal) for 18 hr under $N_2$. After 18.25 hrs (HPLC showed clean conversion after 17.5 hrs), the reaction mixture was cooled to −3 to −4° C. Subsequent dropwise addition of $H_2O_2$ (8.8 mL; 100.14 mmoles) resulted in a high exotherm which subsided only if the addition was stopped. Note the exotherm only occurred during addition of the first 1.3-1.5 mL; addition of the remaining $H_2O_2$ over 15 minutes was not exothermic at all. Upon completion of the addition, the reaction was stirred for 2 hrs at 0-5° C. whereupon HPLC analysis revealed the reaction to be complete and fairly clean (~92.9-93 AP). The reaction was quenched by dropwise addition of cold 60 mL of 1N aqueous $Na_2S_2O_5$ over 12-15 minutes. Note a cooling bath is required as the first 15-20 mL of the quench produced an exotherm resulting in the temperature rising to 17-18° C.; the rest of the addition was endothermic. The mixture was stirred for 20 minutes at 10-15° C. prior to separating the phases. (No peroxides were detected in the organic layer.) The organic layer was washed sequentially with 70 mL of 1N HCl, 65 mL of $H_2O$ and 50 mL of brine prior to drying over 4.5 g of $MgSO_4$. After removal of the desiccant by filtration, the volume was reduced to approximately 30 mL using a rotary evaporator at 25 Torr and bath below 30° C. The residue was redissolved in 65 mL of MTBE; reconcentration to ~30-35 mL produced a slightly hazy residue. Dilution with an additional 35 mL of MTBE and 45 mL of hexanes in 15 mL portions generated a solid. Swirling enhanced formation of white translucent particles during concentration to 40 mL. Further concentration of the residue to dryness yielded 24.5 g of a white solid contaminated with MTBE. Titration of the solid in 40 mL of hexanes produced a seemingly fairly homogeneous suspension which after further dilution with 40 mL hexanes+5 mL of MTBE was collected by filtration. The cake was washed twice with 21 mL each of 95:5 hexanes/MTBE and air-dried for 1 hr on the filter with vacuum suction. After drying RT under vacuum, (R)-2-(4-(6-(4-chlorophenyl)-4-oxothieno[3,2-d]pyrimidin-3(4H)-yl)-2-methoxyphenoxy)-1-cyclopropylethyl bis(2-(trimethylsilyl)ethyl) phosphate (9.64 g; 12.86 mmoles; 95.30% yield) was obtained as a pure white crystalline product with 96.64 AP. $^1H$ NMR δ (400 MHz, $CDCl_3$): 8.10 (s, 1H), 7.64 (d, J=8.8 Hz, 2H), 7.51 (s, 1H), 7.42 (d, J=8.8 Hz, 2H), 7.05 (d, J=8.8 Hz, 1H), 6.94 (d, J=2.7 Hz, 1H), 6.90 (dd, J=8.8, 2.7 Hz, 1H), 4.31-4.20 (m, 2H), 4.21-4.08 (m, 4H), 4.08-4.00 (m, 1H), 3.85 (s, 3H), 1.30-1.18 (m, 1H), 1.13-1.04 (m, 4H), 0.70-0.60 (m, 3H), 0.47-0.38 (m, 1H), 0.02 (2s, 18 H). $^{13}C$ NMR δ (C100 MHz, $DCl_3$): 157.4, 156.8, 151.7, 150.3, 149.1, 148.2, 135.7, 131.6, 130.5, 129.5, 127.7, 123.2, 120.1, 119.2, 114.3, 111.4, 81.1 (d, $J_{C—P}$=5.1 Hz), 71.8 (d, $J_{C—P}$=5.1 Hz), 66.1 (d, $J_{C—P}$=6.4 Hz, 2C), 56.2, 19.6 (2d, $J_{C—P}$=6.4 Hz), 13.1 (d $J_{C—P}$=5.1 Hz), 3.6, 3.0, −1.5. $^{31}P$ NMR δ (162 MHz, $CDCl_3$): −1.11 (m, $J_{P—H}$=7.4 Hz). HPLC: 96.64% API. MS (electrospray, +ions) m/z 749, 751.

C. (R)-2-(4-(6-(4-Chlorophenyl)-4-oxothieno[3,2-d]pyrimidin-3(4H)-yl)-2-methoxyphenoxy)-1-cyclopropylethyl dihydrogen phosphate A mixture of (R)-2-(4-(6-(4-chlorophenyl)-4-oxothieno[3,2-d]pyrimidin-3(4H)-yl)-2-methoxyphenoxy)-1-cyclopropyl-ethyl bis(2-(trimethylsilyl)ethyl) phosphate (35.27 g, 47.06 mmoles), prepared in Part B, and anhydrous $CH_2Cl_2$ (315 mL) in a 500 mL CHEMGLASS® jacketed reactor (glycol) equipped with mechanical stirrer, temperature inlet, nitrogen/vacuum switch inlet, addition funnel and reflux condenser was stirred at 20° C. until dissolution was complete; whereupon, the internal temperature was reduced to −2° C. Once the temperature had stabilized, TFA (30.2 mL; 399.40 mmoles) was added dropwise to the stirred solution resulting in a 1.6° C. temperature rise. The reaction temperature was maintained between −0.5° C. and 1° C. (internal) as aliquots were periodically withdrawn to monitor the reaction progress by HPLC analysis. Immediately following completion of the TFA addition, HPLC analysis revealed the composition to be 9.29% starting bis ester, 44.78% monodeprotection, 42.2% desired product, 1.21% (R)-6-(4-chlorophenyl)-3-(4-(2-cyclopropyl-2-hydroxyethoxy)-3-methoxyphenyl)-thieno[3,2-d]pyrimidin-4(3H)-one and 1.25% of the main side-product. After 64 min, the composition was 0.0% starting ester, 0.62% monodeprotection, 94.36% desired product, 1.52% (R)-6-(4-chlorophenyl)-3-(4-(2-cyclopropyl-2-hydroxyethoxy)-3-methoxyphenyl)-thieno[3,2-d]pyrimidin-4(3H)-one and 2.69% of main side-product. After 95 minutes, the reaction was cooled to ~3° C. prior to the addition of MeOH (28.5 mL) over 5 min. After stirring for 30 min, the reaction was concentrated at 50 mm Hg and 15° C. to a residual volume of ~134 mL. The solution temperature was increased to 19° C. prior to slow addition of 120 mL of MTBE (ca 12 min). Although seeding was begun after addition of ~30 mL, about 42-45 mL of MTBE was added before a white precipitate started to form. After stirring for 2 hours at 19-20° C., the solid was collected by filtration. Both the reactor and the filter cake were washed twice with 120 mL of MTBE/CH$_2$Cl$_2$ 2.5:1 v/v. The very sandy white/off-white material was air-dried for 15 min with vacuum suction before drying overnight in a vacuum oven at 45° C. to obtain 25.58 g of crude product. This material, which contained some TFA by F NMR, was recrystallized by heating 24.3 g of the crude product in 200 mL of THF and 16 mL of water in a CHEMGLASS® jacketed reactor with stirring to 55-57° C. to achieve complete dissolution. The solution was heated at 60° C. for an additional 15 min, cooled to 45° C. over 10 min; whereupon 50 mL of acetone was added over Ca 5 min while maintaining the temperature above 44° C. throughout the addition. Upon completion of addition the faintly cloudy solution was seeded with previously crystallized product. Once rapid crystallization began, an additional 245 mL of acetone over 30 minutes was added maintaining the temperature above 42.5° C. throughout the addition, The resultant thick slurry was cooled to 22° C. (jacket) over ca 60 minutes and stirred for 90 min at 20-21° C. before collecting the solid by filtration. Both the reactor and the filter cake were washed first with 120 mL of acetone/THF 3:1 v/v and then with acetone (110 mL). After air drying for 40 min with vacuum suction, the solid was dried in a vacuum oven at 50° C. for 18 hr to yield 18.96 g of (R)-2-(4-(6-(4-chlorophenyl)-4-oxothieno[3,2-d]pyrimidin-3(4H)-yl)-2-methoxyphenyloxy)-1-cyclopropylethyl dihydrogen phosphate (99.2% ee, 99.4% purity in 73% yield). M.P. 166° C. $^1$H NMR (500 MHz, DMSO-d$_6$) δ ppm 0.41 (m, 2H), 0.52 (m, 2H)$_3$, 1.26 (m, 1H), 3.82 (m, 1H), 4.20 (d, 2H, J=4.29 Hz), 3.80 (s, 3H), 7.06 (dd, 1H, J=8.57, J=2.34 Hz), 7.15 (d, 1H, J=8.57 Hz), 7.22 (d, 1H, J=2.34 Hz), 7.58 (d, 2H, J=8.57 Hz), 7.93 (2H, J=8.57 Hz), 7.98 (s, 1H), 8.40 (s, 1H). $^1$H NMR (126 MHz, DMSO-d) δ ppm 2.4, 3.1, 13.1, 56.0, 71.0, 77.9, 112.2, 113.1, 119.8, 121.9, 122.1, 128.0, 129.4, 130.1, 131.3, 134.4, 148.4, 149.1, 149.6, 149.9, 156.2, 157.5. $^{31}$P NMR δ (162 MHz, DMSO-d$_6$): −0.75. HPLC: 95.4% API; 0.69%. LC/MS: m/e 549.1 (M+H); 4 min gradient. High Res. Mass: C$_{24}$H$_{23}$O$_7$N$_2$ClPS calc. 549.06522; exp. 549.06531.

Chiral HPLC: Optical purity was assessed by HPLC chromatography at 20° C. using a CHIRALCEL® OJ-RH, 150× 4.6 mm ID; 5 μm column for which the mobile phase was 100% methanol with 0.1% phosphoric acid with a flow rate of 0.5 mL/min. Under these conditions the S enantiomer eluted in 8 minutes followed by the desired R enantiomer at 10 min.

Example 4

(S)—((R)-2-(4-(6-(4-Chlorophenyl)-4-oxothieno[3,2-d]pyrimidin-3(4H)-yl)-2-methoxyphenoxy)-1-cyclopropylethyl) 2-amino-3-methylbutanoate

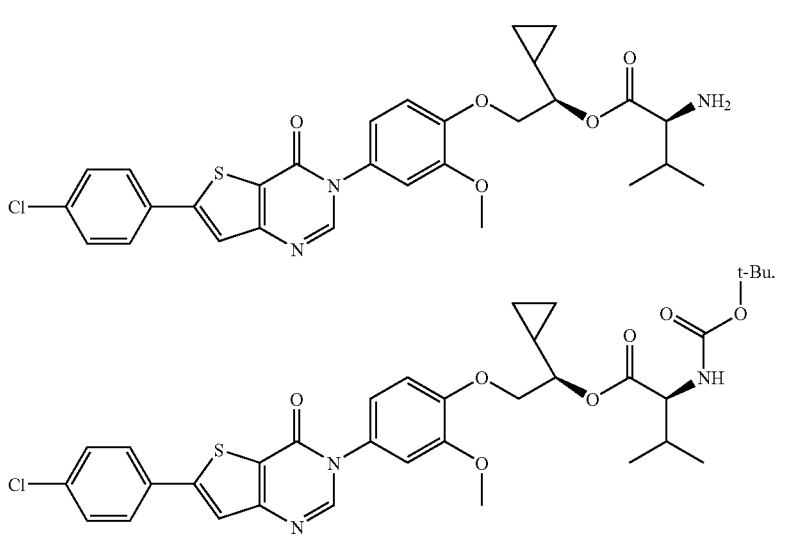

A mixture of (R)-6-(4-chlorophenyl)-3-(4-(2-cyclopropyl-2-hydroxyethoxy)-3-methoxyphenyl)-thieno[3,2-d]pyrimidin-4(3H)-one described in Example 1 (1.3 g, 2.33 mmol), diisopropylcarbodiimide (0.88 g, 6.99 mmol), 4-dimethylaminopyridine (142 mg, 1.16 mmol) and N-(t-butoxycarbonyl)-L-valine (1.52 g, 6.99 mmol) in CH$_2$Cl$_2$ (10 mL) was stirred at rt for 19 h. By LCMS analysis no starting alcohol remained. The suspension was diluted with CH$_2$Cl$_2$ and washed with aq NaHCO$_3$. After extracting the aqueous layer with CH$_2$Cl$_2$, the combined organic layers were washed sequentially with water and brine, dried over Na$_2$SO$_4$, filtered and the filtrate concentrated under reduced pressure. The residue was purified by flash chromatography (silica gel, EtOAC/hexane 0 to 40% gradient) to afford the title compound (1.12 g) as a white solid. $^1$H NMR (CDCl$_3$) δ 0.41-0.46 (m, 1H), 0.49-0.53 (m, 1H), 0.58-0.63 (m, 1H), 0.64-0.68 (m, 1H), 0.925 (d, J=7 Hz), 3H), 0.99 (d, J=7 Hz), 1.16-1.19 (m, 1H), 1.44 (s, 9H), 2.19-2.23 (m, 1H), 3.86 (s, 3H), 4.23-4.32 (m, 3H), 4.67-4.71 (m, 1H), 5.06 (d, J=2 Hz, 1H), 6.92-6.95

(m, 2H), 7.04 (d, J=2 Hz, 1H), 7.26 (s, 2H), 7.45 (d, J=2 Hz), 7.54 (s, 1H), 7.66 (d, J=2 Hz, 2H), 8.16 (s, 1H). LCMS (ES): m/z 669 [M+H].

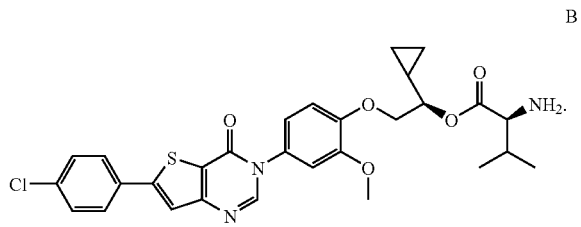

The BOC valine ester from part A (1.12 g, 1.67 mmol) was dissolved in a 1:2 mixture of TFA/CH$_2$Cl$_2$ (17 mL). By HPLC analysis after 1 hr at 20° C., the reaction was complete whereupon the volatiles were removed under vacuum. The residue upon dissolution in CH$_2$Cl$_2$ was washed 2× with aq NaHCO$_3$/Na$_2$CO$_3$ followed by brine prior to drying over Na$_2$SO$_4$. Upon concentration, 900 mg (94%) of the title compound was obtained. Further purification was achieved by flash chromatography (silica gel, MeOH/CH$_2$Cl$_2$, 0 to 10% gradient) to afford the title compound (0.87 g) as a white solid. $^1$H NMR (CDCl$_3$) δ 0.41-0.45 (m, 1H), 0.50-0.54 (m, 1H), 0.58-0.63 (m, 1H), 0.64-0.67 (m, 1H), 0.94 (d, J=7 Hz, 3H), 1.01 (d, J=7 Hz), 1.16-1.19 (m, 1H), 2.07-2.10 (m, 1H), 3.36 (d, J=41 Hz, 1H), 3.87 (s, 3H), 4.24-4.31 (m, 2H), 4.68-4.72 (m, 1H), 6.92-6.95 (m, 2H), 7.03 (d, J=2 Hz, 1H), 7.26 (s, 2H), 7.44 (d, J=2 Hz), 7.53 (s, 1H), 7.66 (d, J=2 Hz, 2H), 8.14 (s, 1H). LCMS (ES): m/z 569 [M+H]$^+$.

Example 5

(R)-2-(4-(6-(4-Chlorophenyl)-4-oxothieno[3,2-d]pyrimidin-3(4H)-yl)-2-methoxy-phenoxy)-1-cyclopropylethyl 2-aminoacetate, hydrochloride salt

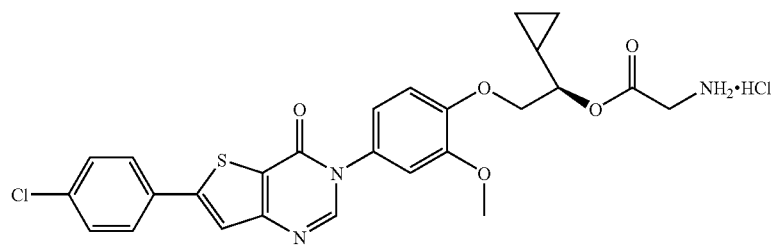

To a mixture of the (R)-6-(4-chlorophenyl)-3-(4-(2-cyclopropyl-2-hydroxyethoxy)-3-methoxyphenyl)-thieno[3,2-d]pyrimidin-4(3H)-one described in Example 1 (300 mg, 0.640 mmol), 2-(tert-butoxycarbonylamino)acetic acid (168 mg, 0.960 mmol), and DMAP (65 mg, 0.532 mmol) in CH$_2$Cl$_2$ (20 mL) was added diisopropylcarbodiimide (150 μL, 0.963 mmol) dropwise at 25° C. The resulting mixture was stirred for 2 h at 25° C. Evaporation followed by flash chromatography (120 g, 0% to 100% EtOAc-Hexanes) yielded the desired N-Boc glycine ester (477 mg, 0.762 mmol, 119% yield) as a colorless solid containing 15 mole % of diisopropylurea. HPLC Method: Gradient solvent system from 100% A:0% B to 0% A:100% B (A=90% H$_2$O/10% MeOH+0.2% H$_3$PO$_4$; B=90% MeOH/10% H$_2$O+0.2% H$_3$PO$_4$) for 4 min; detection at 220 mm. YMC S3 ODS 4.6×50 mm Ballistic column; Retention time=3.61 min, 100%.

Without further purification, the N-Boc glycine ester (379 mg, 0.605 mmol) was added to 4N HCl in dioxane (10 mL, 40.0 mmol). After stirring for 3 h, the mixture was diluted with MeOH (5 mL) and filtered. The filter cake was washed with Et$_2$O (50 mL) to yield the HCl salt of the title compound (291 mg, 0.52 mmol, 85% yield) as an off-white solid. M.P. 218-220° C. $^1$H NMR (DMSO-d$_6$, 400 MHz): δ 0.38-0.48 (m, 1H), 0.49-0.64 (m, 3H), 1.18-1.30 (m, 1H), 3.3-3.42 (m, 2H), 3.77 (s, 3H), 3.78-4.0 (m, 2H), 4.2-4.32 (m, 2H), 4.65-4.74 (m, 1H), 7.06 (dd, J=8.85, 2.64 Hz, 1H), 7.15 (d, J=8.8 Hz, 1H), 7.22 (d, J=2.2 Hz, 1H), 7.58 (d, J=8.35 Hz, 2H), 7.93 (d, J=8.8 Hz, 2H), 7.99 (s, 1H). LC-MS: 526.1 [M+H]$^+$. HPLC: SunFire C18 3.5 μM, 4.6×150 mm, 10% to 100% over 10 min and 100-100% over next 5 min; flow rate=1 mL/min; Solvent A=0.05% TEA in H$_2$O:CH$_3$CN (95:5), Solvent B=0.05% TEA in H$_2$O:CH$_3$CN (5:95). R$_t$=7.46 min, purity>99%.

Example 6

(S)—((R)-2-(4-(6-(4-Chlorophenyl)-4-oxothieno[3,2-d]pyrimidin-3(4H)-yl)-2-methoxyphenoxy)-1-cyclopropylethyl) 2-aminopropanoate, hydrochloride salt

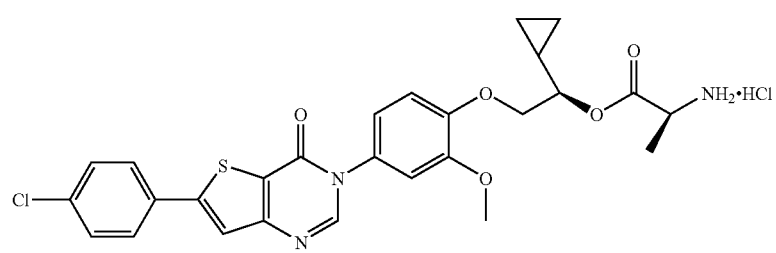

The title compound was prepared in a manner analogous to that described for Example 5 except that Boc-L-alanine was used in place of Boc-glycine. $^1$H NMR (methanol-$d_4$, 400 MHz): δ 0.45-0.58 (m, 2H), 0.6-0.75 (m, 2H), 1.22-1.34 (m, 1H), 1.58 (d, J=7.5 Hz, 3H), 3.87 (s, 3H), 4.07 (br q, J=7.0 Hz, 2H), 4.35-4.42 (m, 2H), 4.72-4.80 (m, 1H), 7.04 (dd, J=8.6, 2.4 Hz, 1H), 7.14-7.20 (m, 2H), 7.52 (d, J=8.35 Hz, 2H), 7.73 (s, 1H), 7.83 (d, J=8.35 Hz, 2H), 8.39 (s, 1H). LC-MS: 540.4 [M+H]$^+$. HPLC: SunFire C18 3.5 M, 4.6×150 mm, 10% to 100% over 10 min and 100-100% over next 5 min; flow rate=1 mL/min; Solvent A 0.05% TFA in H$_2$O:CH$_3$CN (95:5), Solvent B=0.05% TFA in H$_2$O:CH$_3$CN (5:95). R$_f$=7.62 min, purity=98.7% (Detector I).

Example 7

(R)-5-(2-(4-(6-(4-Chlorophenyl)-4-oxothieno[3,2-d]pyrimidin-3(4H)-yl)-2-methoxyphenoxy)-1-cyclopropylethoxy)-5-oxopentanoic acid

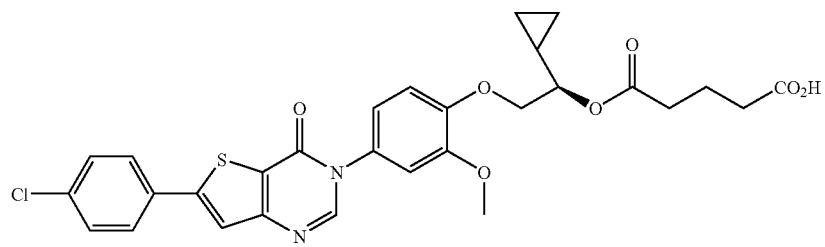

A mixture of glutaric anhydride (73.0 mg, 0.640 mmol), (R)-6-(4-chlorophenyl)-3-(4-(2-cyclopropyl-2-hydroxyethoxy)-3-methoxyphenyl)thieno[3,2-d]pyrimidin-4(3H)-one (60 mg, 0.128 mmol) prepared in Example 1 and 4-pyrrolidinopyridine (18.96 mg, 0.128 mmol) in CH$_2$Cl$_2$ (4 mL) was stirred at 40° C. for 25 hours. LC-MS indicated about 35% conversion. Additional portions of glutaric anhydride (130 mg) and 4-pyrrolidinopyridine (20 mg) were added. After stirring at 40° C. for another 16h, conversion was complete according to HP LC. The mixture was cooled to RT, diluted with CH$_2$Cl$_2$ (10 mL), washed with 1N HCl, brine-, died (Na$_2$SO$_4$), filtered, and evaporated to yield a white solid, which was purified by Preparative HPLC (PHENOMENEX® Luna Axia 5μ C18 30×100 mm; 10 min gradient from 40% A: 60% B to 0% A:100% B (A=90% H$_2$O/10% MeOH+0.1% TFA); (B=90% MeOH/10% H$_2$O+0.1% TFA); detection at 220 inn) to yield impure title compound (58 mg, 78%) as a white solid. The product was further purified by Preparative HPLC using CH$_3$CN-system (PHENOMENEX® Luna Axia 5® C18 30×100 mm; 10 min gradient from 40% A: 60% B to 0% A: 100% B (A 90% H$_2$O/10% CH$_3$CN+0.1% TFA); (B=90% CH$_3$CN/10% H$_2$O+0.1% TFA); detection at 220 nm) to yield the title compound (40 mg, 0.069 mmol, 53.6% yield) as a white solid. $^1$H NMR (CDCl$_3$, 400 MHz): δ 0.33-0.43 (m, 1H), 0.45-0.55 (m, 1H), 0.55-0.68 (m, 2H), 1.06-1.18 (m, 1H), 1.85-1.95 (m, 2H), 2.30-2.45 (m, 4H), 3.86 (s, 3H), 4.23-4.35 (m, 2H), 4.64-4.73 (m, 1H), 6.87-6.96 (m, 2H), 7.03 (d, J=7.9 Hz, 2H), 7.44 (d, J=8.35 Hz, 2H), 7.53 (s, 1H), 7.65 (d, J=8.35 Hz, 2H), 8.24 (s, 1H). LC-MS, [M+H]-4=583.5. HPLC Method: Gradient solvent system from 100% A:0% B to 0% A:100% B (A=90% H$_2$O/10% MeOH+0.2% H$_3$PO$_4$; B=90% MeOH/10% H$_2$O+ 0.2% H$_3$PO$_4$) for 4 min; detection at 220 nm. YMC S3 ODS 4.6×50 mm Ballistic column; Retention time=4.35 min.

Example 8

1-((4-(6-(4-Chlorophenyl)-4-oxothieno[3,2-d]pyrimidin-3(4H)-yl)-2-methoxyphenoxy)methyl)-3,3-difluorocyclobutyl dihydrogen phosphate

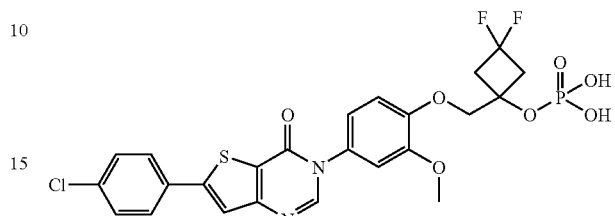

A. Dibenzyl 1-((4-(6-(4-chlorophenyl)-4-oxothieno[3,2-d]pyrimidin-3(4H)-yl)-2-methoxyphenoxy)methyl)-3,3-difluorocyclobutyl phosphate

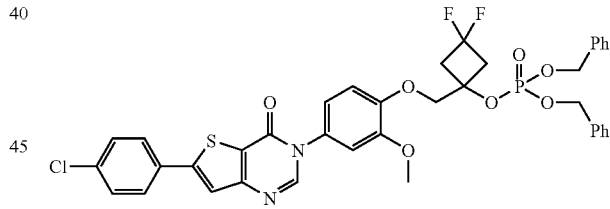

A mixture of 6-(4-chlorophenyl)-3-(4-((3,3-difluoro-1-hydroxycyclobutyl)methoxy)-3-methoxyphen-yl)thieno[3,2-d]pyrimidin-4(3H)-one (1.01 g, 2.000 mmol) described in Example 2, dibenzyl diisopropylphosphoramidite (2.073 g, 6.00 mmol) and 1H-1,2,4-triazole (0.414 g, 6.00 mmol) in 1,2-dichloroethane (30 mL) was heated at reflux temperature. After 1 h, the mixture was cooled to RT; whereupon, 2 mL 50% H$_2$O$_2$ was added. After stirring for 15 minutes at RT, the mixture was diluted with CH$_2$Cl$_2$, washed sequentially with water, 5% aq. sodium thiosulfate and water. The organic layer was dried over MgSO$_4$, concentrated and the crude product was subjected to flash chromatography (silica gel/hexane-EtOAc 100:0 to 0:100 gradient) to afford dibenzyl 1-((4-(6-(4-chlorophenyl)-4-oxothieno[3,2-d]pyrimidin-3(4H)-yl)-2-methoxyphenoxy)methyl)-3,3-difluorocyclobutyl phosphate (1.3 g, 1.699 mmol, 85% yield). $^1$H NMR (400 MHz, chloroform-d) δ ppm 8.10 (1 H, s), 7.66 (2 H, d, J=8.56 Hz), 7.54 (1 H, s), 7.45 (2H, d, J=8.56 Hz), 7.28-7.40 (10 H, m), 6.95 (1 H, d, J=8.56 Hz), 6.92 (1 H, d, J=2.27 Hz), 6.87 (1 H, dd, J=8.31, 2.27 Hz), 5.08 (4 H, dd, J=7.81, 1.26 Hz), 4.32 (2 H, s), 3.76 (3 H, s), 2.89-3.30 (4 H, m).

B. 1-((4-(6-(4-Chlorophenyl)-4-oxothieno[3,2-d]pyrimidin-3(4H)-yl)-2-methoxyphenoxy)methyl)-3,3-difluorocyclobutyl dihydrogen phosphate

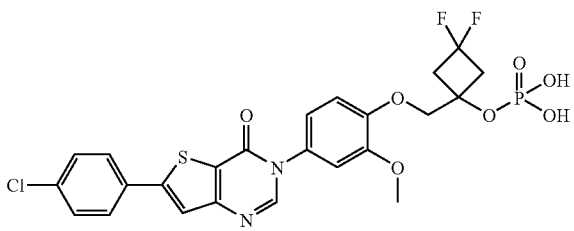

Dibenzyl 1-((4-(6-(4-chlorophenyl)-4-oxothieno[3,2-d]pyrimidin-3 (44)-yl)-2-methoxyphenoxy)methyl)-3,3-difluorocyclobutyl phosphate (1.3 g, 1.699 mmol) prepared in Part A was dissolved in 5 mL of neat TFA. After 3 h at RT, the reaction was concentrated and reconcentrated from MeOH (3×) using a rotary evaporator. The residue was triturated from EtOH to afford white solid 1-((4-(6-(4-chlorophenyl)-4-oxothieno-[3,2-d]pyrimidin-3(4H)-yl)-2-methoxyphenoxy)methyl)-3,3-difluorocyclobutyl dihydrogen phosphate (0.985 g, 1.684 mmol, 99% yield). M.P. 219° C. $^1$H NMR (400 MHz, DMSO-d$_6$) δ 8.40 (1 H, s), 7.98 (1 H, s), 7.92 (2 H, d, J=8.3 Hz), 7.57 (2 H, d, J=8.3 Hz), 7.23 (1 H, d, J=1.8 Hz), 7.15 (1 H, d, J=8.8 Hz), 7.07 (1 H, d, J=8.1 Hz), 4.27 (2 H, s), 3.79 (3 H, s), 3.21 (2 H, q, J=14.4 Hz), 2.94-3.10 (2 H, m). $^{13}$C NMR (126 MHz, CDCl$_3$) δ ppm 157.41, 156.05, 149.81, 149.42, 149.30, 148.08, 131.2, 130.63, 129.27, 127.83, 122.0, 121.72, 119.73, 118.21 (t, J=270.9 Hz), 114.1, 112.28, 72.2 (m), 69.32 (ddd, J=18.5, 12.0, 6.9 Hz), 56.0, 44.32 (m) LCMS; 585 (M+H).

Example 9

1-((4-(6-(4-Chlorophenyl)-4-oxothieno[3,2-d]pyrimidin-3(4H)-yl)-2-methoxyphenoxy)methyl)-3,3-difluorocyclobutyl 2-aminoacetate

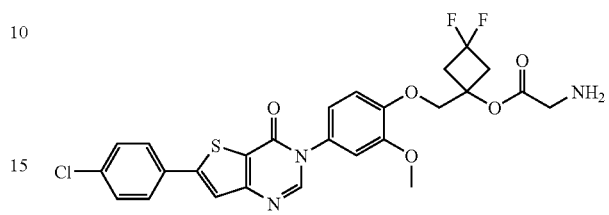

1-(3-Dimethylaminopropyl)-3-ethylcarbodiimide hydrochloride (3.80 g, 19.80 mmol) was added to a mixture of 6-(4-chlorophenyl)-3-(4-((3,3-difluoro-1-hydroxycyclobutyl)-methoxy)-3-methoxyphenyl)thieno[3,2-d]pyrimidin-4(3H)-one (2.0 g, 3.96 mmol), prepared in Example 2, Boc-glycine (3.47 g, 19.80 mmol) and 4-(pyrrolidin-1-yl)pyridine (2.94 g, 19.80 mmol) in CH$_2$Cl$_2$ (50 mL). The mixture was refluxed with stirring for 15 min, diluted with CH$_2$Cl$_2$, washed sequentially with cold 10% aq. H$_2$SO$_4$ and sat. NaHCO$_3$. The organic layer was dried (MgSO$_4$) and concentrated to give white solid (3.8 g). After dissolution in CH$_2$Cl$_2$ (30 mL) and addition of TFA (15 mL), the solution remained at RT for 15 min. The reaction mixture was then concentrated, partitioned between CH$_2$Cl$_2$ and 5% aq. Na$_2$CO$_3$ solution. The organic layer was dried (MgSO$_4$) and concentrated under vacuum. The crude product was flash chromatographed (silica gel/CH$_2$Cl$_2$-iPrOH 100.0 to 80:20 gradient) to afford 1-((4-(6-(4-chlorophenyl)-4-oxothieno[3,2-d]pyrimidin-3(4H)-yl)-2-methoxyphenoxy)methyl)-3,3-difluorocyclobutyl 2-aminoacetate (2.2 g). $^1$H NMR (400 MHz, chloroform-d) δ ppm 8.13 (1 H, s), 7.66 (2 H, d, J=8.56 Hz), 7.53 (1 H, s), 7.45 (2 H, d, J=8.56 Hz), 7.03 (1 H, d, J=8.56 Hz), 6.97 (1 H, d, J=2.52 Hz), 6.92 (1 H, dd, J=8.31, 2.27 Hz), 4.44 (2 H, s), 3.88 (3 H, s), 3.43 (2 H, s), 3.06-3.36 (2 H, m), 2.85-3.07 (2 H, m). LCMS: 562 (M+H).

Example 10

(S)-1-((4-(6-(4-Chlorophenyl)-4-oxothieno[3,2-d]pyrimidin-3(4H)-yl)-2-methoxyphenoxy)methyl)-3,3-difluorocyclobutyl 2-aminopropanoate, hydrochloride salt

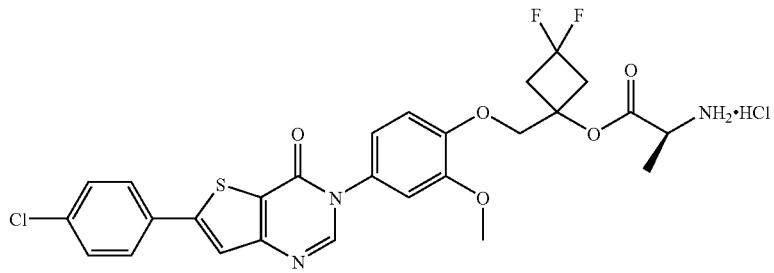

A. (S)-1-((4-(6-(4-Chlorophenyl)-4-oxothieno[3,2-d]
pyrimidin-3(4H)-yl)-2-methoxyphenoxy)methyl)-3,
3-difluorocyclobutyl 2-(tert-butoxycarbonylamino)
-propanoate

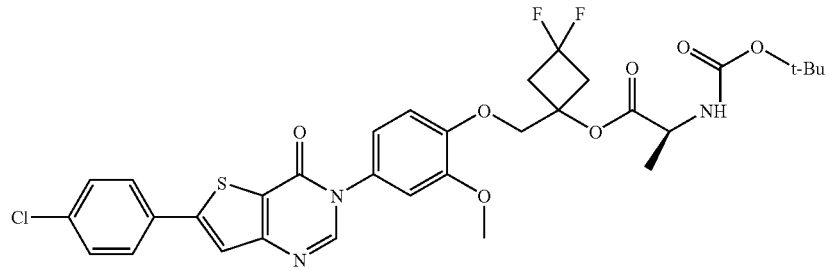

A mixture of Boc-alanine (94 mg, 0.495 mmol), 6-(4-chlorophenyl)-3-(4-((3,3-difluoro-1-hydroxycyclobutyl)methoxy)-3-methoxyphenyl)thieno[3,2-d]pyrimidin-4(3H)-one (50 mg, 0.099 mmol) from Example 2,4-pyrrolidinopyridene (14.68 mg, 0.099 mmol) and N,N'-diisopropylcarbodiimide (0.077 mL, 0.495 mmol) in CH$_2$Cl$_2$ (4 mL) was stirred at 40° C. in a sealed tube for 18 hours. After cooling to RT and removal of the volatiles under vacuum, the crude product was subjected to gradient chromatography (silica gel/EtOAc/hexane 0 to 30%) to afford (S)-1-((4-(6-(4-chlorophenyl)-4-oxothieno[3,2-d]pyrimidin-3(4H)-yl)-2-methoxyphenoxy)methyl)-3,3-difluorocyclobutyl 2-(tert-butoxycarbonylamino)propanoate (59 mg, 0.087 mmol, 88% yield) as off-white solid. $^1$H NMR (400 MHz, CDCl$_3$) δ ppm 8.13 (1 H, s), 7.66 (2 H, d), 7.54 (1 H, s), 7.46 (2 H, d), 6.87-7.06 (3 H, m), 4.96 (1 H, br. s.), 4.34-4.48 (2H, m), 4.20-4.34 (1 H, m), 3.87 (3 H, s), 3.09-3.24 (2 H, m), 2.97 (2 H, broad s.), 1.45 (9 H, s), 1.38 (3 H, d, J=7.30 Hz). LC-MS: 2.72 min 677 (M+H). Luna 5 u C18 30×4.6 mm ID, flow rate=4 ml/min., gradient=0% A to 100% B in 2 min., A=90% H$_2$O/10% MeOH/0.1% TFA, B=10% H$_2$O/90% MeOH/0.1% TFA).

B (S)-1-((4-(6-(4-Chlorophenyl)-4-oxothieno[3,2-d]
pyrimidin-3(4H)-yl)-2-methoxyphenoxy)methyl)-3,
3-difluorocyclobutyl 2-aminopropanoate, hydrochloride salt A mixture of (S)-1-((4-(6-(4-chlorophenyl)-4-oxothieno[3,2-d]pyrimidin-3(4H)-yl)-2-methoxyphenoxy)methyl)-3,3-difluorocyclobutyl 2-(tert-butoxycarbonylamino)-propanoate from Part A (59 mg, 0.087 mmol) in 25% TFA/CH$_2$Cl$_2$ (4 mL) was stirred at RT for 30 min. After removal of the volatiles under vacuum, the crude product was purified by prep-HPLC (PHENOMENEX® Axia, Luna 5 micron 30×100 mm, flow rate=40 ml/min., gradient 0% A to 100% B in 10 min., A=90% H$_2$O/10% MeOH/0.1% TFA, B=10% H$_2$O/90% MeOH/0.1% TFA). The desired fractions were concentrated and dried under high vacao prior to addition of aq. saturated NaHCO$_3$ (6 ml) and extraction with CH$_2$Cl$_2$ (2×10 ml). The combined CH$_2$Cl$_2$ layers were dried over Na$_2$SO$_4$ and concentrated prior to conversion of the free base (42 mg, 0.073 mmol) to the HCl salt by dissolution in CH$_2$Cl$_2$ (2 ml) and addition of 1.0 M HCl (0.079 mL, 0.079 mmol)/MeOH (2 ml) at −30° C. The HCl salt was then concentrated and was dried under high vacuum to yield (S)-1-((4-(6-(4-chlorophenyl)-4-oxothieno[3,2-d]pyrimidin-3(4H)-yl)-2-methoxyphenoxy)methyl)-3,3-difluorocyclobutyl 2-aminopropanoate (41.94 mg, 0.073 mmol, 83% yield) as white solid. $^1$H NMR (400 MHz, MeOD) δ ppm 8.27 (1H, s), 7.73 (2 H, d)$_3$ 7.63 (1 H, s), 7.43 (2 H, d), 7.02-7.15 (2 H, m), 6.94 (1 H, dd, J=8.56, 2.52 Hz), 4.41 (2 H, d, J=3.02 Hz), 3.91-4.02 (1 H, m), 3.78 (3 H, s), 2.87-3.18 (4 H, m), 1.44 (3 H, d, J=7.30 Hz). LC-MS: 2.33 min 576 (M+H). Luna 5 u C18 30×4.6 mm ID, flow rate=4 ml/min., gradient=0% A to 100% B in 2 min., A=90% H$_2$O/10% MeOH/0.1% TFA, B=10% H$_2$O/90% MeOH/0.1% TFA).

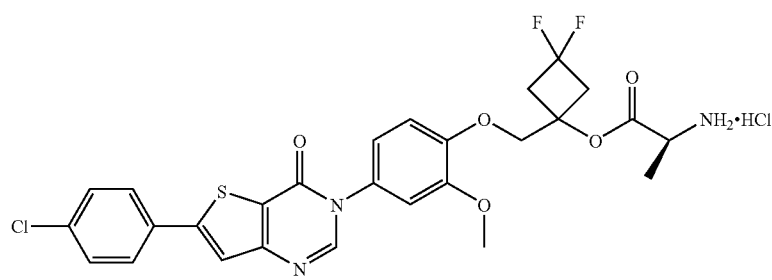

Example 11

5-(1-((4-(6-(4-Chlorophenyl)-4-oxothieno[3,2-d]pyrimidin-3(4H)-yl)-2-methoxyphenoxy)methyl)-3,3-difluorocyclobutoxy)-5-oxopentanoic acid, sodium salt

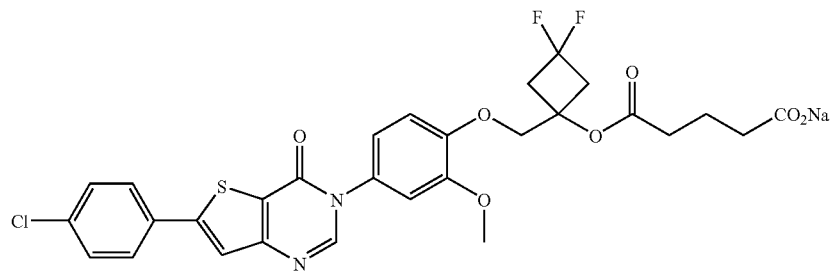

A mixture of glutaric anhydride (56.5 mg, 0.495 mmol), 6-(4-chlorophenyl)-3-(4-((3,3-difluoro-1-hydroxycyclobutyl)methoxy)-3-methoxyphenyl)thieno[3,2-d]pyrimidin-4(3H)-one from Example 2 (50 mg, 0.099 mmol) and 4-pyrrolidinopyridine (14.68 mg, 0.099 mmol) in $CH_2Cl_2$ (4 mL) was stirred at 40° C. for 18 hours. After cooling and removal of the volatiles under vacuum, the crude product was purified by prep-HPLC (PHENOMENEX® Axia, Luna 5 micron 30×100 mm, flow rate=40 ml/min., gradient=0% A to 100% B in 10 min., Solvent A=90% $H_2O$/10% MeCN.1°% TFA, Solvent B=10% $H_2O$/90% MeCN.1% TFA). The desired fractions were combined, concentrated and dried under high vacao to yield the pure free acid (37 mg, 0.60 mmol).

If desired, the corresponding sodium salt can be generated by addition of 0.5M aq. $NaHCO_3$ (0.131 mL, 0.065 mmol) to a THF solution (2 mL) containing the acid (37 mg, 0.60 mmol). The solution was then concentrated and dried under high vacuum to yield sodium 5-(1-((4-(6-(4-chlorophenyl)-4-oxothieno[3,2-d]pyrimidin-3(4H)-yl)-2-methoxyphenoxy)methyl)-3,3-difluorocyclobutoxy)-5-oxopentanoate (37.59 mg, 0.061 mmol, 61.3% yield) as off-white solid. $^1$H NMR (400 MHz, MeOD) δ ppm 8.28 (1 H, s), 7.67-7.81 (2 H, m), 7.62 (1 H, s), 7.37-7.47 (2 H, m), 7.01-7.11 (2 H, m), 6.92 (1 H, dd, J=8.44, 2.39 Hz), 4.33 (2 H, s), 3.78 (3 H, s), 2.94-3.11 (2 H, m), 2.78-2.95 (2 H, m), 2.27 (2 H, J J=7.5 Hz), 2.13 (2 H, t, J=7.43 Hz), 1.68-1.84 (2 H, m). LC-MS: 2.59 min 619 (M+H). Luna 5μ C18 30×4.6 mm ID, flow rate=4 ml/min., gradient=0% A to 100% B in 2 min., A=90% $H_2O$/10% MeOH/0.1% TFA, B=10% $H_2O$/90% MeOH/0.1% TFA).

Assay and Biological Evaluation

Compounds of the present invention, namely Compounds IA and IB of the invention, and Compounds a to f (prepared as described in U.S. Patent Publication No. 2007/0093509 A1 published Apr. 26, 2007), were initially characterized in an in vitro binding assay to determine their $K_i$ or ability to antagonize binding of a peptide agonist to the human melanin concentrating hormone receptor (MCHR1).

Radioligand Binding Assay for Assessment of MCHR1 Activity

Membranes from stably transfected HEK-293 cells expressing a mutated (E4Q, A5T) hMCHR1 receptor were prepared by dounce homogenization and differential centrifugation. Binding experiments were carried out with 0.5-1.0 ug of membrane protein incubated in a total of 0.2 ml in 25 mM HEPES (pH 7.4) with 10 mM MgCl2, 2 mM EGTA, and 0.1% BSA (Binding Buffer) for 90 min. For competition binding assays, reactions were carried out in the presence of with 0.06-0.1 nM [Phe$^{13}$, [$^{125}$I]Tyr$^{19}$]-MCH and increasing concentrations of unlabeled test molecules. Reactions were terminated by rapid vacuum filtration over 96 well-GFC Unifilter plates pre-coated with 0.075 ml binding buffer containing 1% BSA, and washed 3 times with 0.4 ml of Phospho-buffered Saline (pH 7.4) containing 0.01% TX-100, Filters were dried, 0.05 ml MicroScint 20 was added to each well and radioactivity was subsequently quantified by scintillation counting on a TOPCOUNT® microplate scintillation counter (Packard). Inhibitory constants were determined by nonlinear least squares analysis using a four parameter logistic equation.

Compounds exhibiting Ki values of 20 mM or less were selected for further characterization for metabolic stability versus rat microsomal oxidative degradation mediated by cytochrome P450 enzymes. Compounds exhibiting less than 10% degradation were further evaluated in a rat PK model to assess oral bioavailability and ability to access the CNS. For the compounds of the present invention IA and IB and a to f, solubility limited absorption severely curtailed oral exposure unless the compounds (IA and IB and a to f) were administered as a pro-drug which for this evaluation was an amino acid ester, namely valine and glycine, respectively. The L-valine ester prodrug was employed for the comparative in vivo studies with the subset containing IA, c, d and e; the glycine ester prodrug was utilized for the subset containing IS, a, b and f. After oral administration of a 10 mg/kg dose of the pro-drug ester to rats, criteria for further evaluation were a brain to plasma ratio of 0.2 to 3 and an 8 hr AUC greater than 3 micromole*hr of the bio-active substance. The subset of compounds meeting this criteria were subsequently evaluated in a four day efficacy model entailing daily administration of the ester pro-drug to young growing male rats. Compounds producing dose dependent weight loss which exceeded 5% weight loss when administered at 30 mg/kg or less were further characterized using hepatocytes obtained from rat, dog, primate and humans to determine relative clearance rates as well as to ascertain which species would best predict the human clearance. After the dog was established as being most predictive for human PK, the half-life in dog was utilized to project the clinical half-life of the active compounds.

Compounds Tested

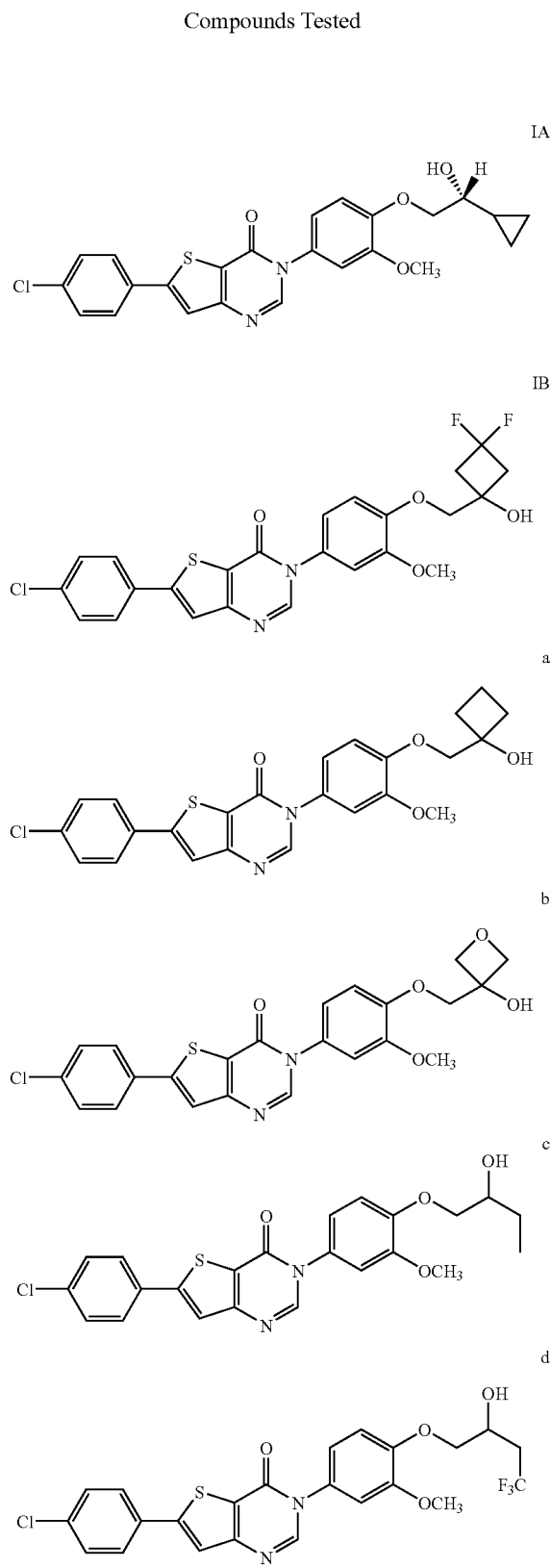

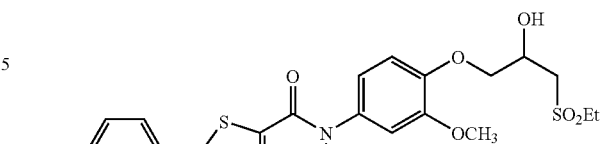

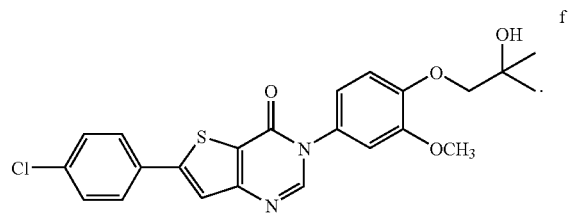

FLOW SCHEME FOR CHARACTERIZATION
OF MCHR1 ANTAGONIST

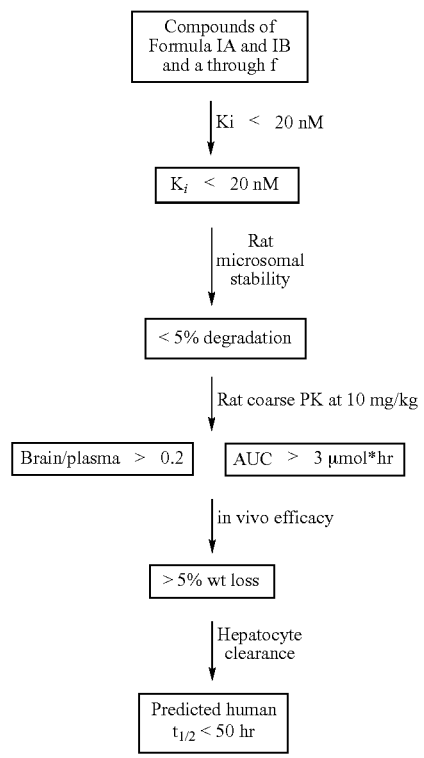

Despite the similarity in structure to compounds IA and IB (the compounds of the invention), compounds a to f, illustrated above, failed to meet all of the criteria.

Only compounds IA and IB of the invention met the selection criteria for each of these assays. For compound f hepatocyte clearance was very slow for both dog and human. Subsequent full PK study in dog revealed the half-life in dogs to exceed 200 hr. Given that the human half-life was projected to be equally long if not longer, progression of compound f was deemed to be undesirable since compounds with half-lives exceeding a week greatly complicate and increase expense as well as raise safety concerns during clinical studies.

Moreover, subsequent studies with rats administered compound f at 30 mg/kg for a month revealed that the animals developed obstructive hepatic biliary lesions. Further investigation established that the toxic agent was a metabolite arising from in vivo oxidative hydroxylation of the alkyl chain containing the tertiary carbinol moiety of compound f. When administered to rats for a month at doses up to 300 mg/kg, neither compound IA nor compound IB induced biliary lesion formation since a comparable metabolic transformation cannot occur.

The room was maintained at 72° F. and 50% humidity, and a 12/12 light dark cycle with lights out at 1600 hours. The rats were conditioned for 5 days prior to the start of the study to having a choice of foods. A normal chow (HARLAN TEKLAD®, 2018) that contains 18% protein, 5% fat and 73% carbohydrate and a high fat high sugar diet (Research Diets (D2327)) that contains 20% protein, 40% fat and 40% carbohydrate where the carbohydrate is entirely sucrose and the fat is soybean and coconut oil. Studies have revealed that rats exhibit a high preference for the high fat coconut oil. Studies

| Compound No. | Human Ki (nM) | Rat Microsomal Stability | Brain:Plasma | Rat PK AUC (10 mg/kg) | Efficacy at 30 mg/kg (weight loss in young growing rats) | Dog Half-life (hr) | Predicted Human Half-life | Formation of Biliary Lesions |
|---|---|---|---|---|---|---|---|---|
| IA | 10 | 92% | 0.9 | 24.5 | 6.4% | 32 hr | 35 hr | No |
| IB | 18 | 95% | 2.5 | 38 | 7.9% | 16 hr | 18-30 hr | No |
| a | 10 | 20% | | 1.3 | | | | |
| b | 9 | 40% | 1.1 | 35 | 0 | | | Yes |
| c | 12 | 60% | 3.2 | 14.5 | 4.1 | | | No |
| d | 11 | 100% | 1.1 | 20 | 3.2 | | | No |
| e | 8 | 100% | 0.09 | 46 | 4.5 | | | No |
| f | 12 | 98% | 2 | 45 | 8.2 | >200 hr | >200 hr | Yes |

Compounds IA and IB also exhibited human hepatocyte clearance rates that approximated that of dog; however, the half-life in dogs was under 20 hr. As a consequence the projected human half-life for these two compounds was predicted to be 20 to 40 hr. Accordingly, compounds IA and IB exhibit surprisingly superior pharmacodynamic, pharmacokinetic and safety profiles.

Evaluation of Prodrugs

The relative ability of the prodrug to enhance exposure (bioavailability) was assessed in an eight hour PK study using cannulated SPRAGUE DAWLEY® (CD, Charles River Breeding Laboratory) rats. The compounds (parent and prodrug esters) were administered p.o. at 2.0 ml/kg as a suspension in 0.5% methyl cellulose, 0.1% Tween 80 in water at 10 mg/kg p.o. Blood samples were taken at 1, 2, 4 and 8 hr. After determination of parent concentration, an AUC was calculated for the eight hour study.

| Compound Administered | AUC of Parent (µM*hr) |
|---|---|
| | AUC of IA |
| Example 3 | 24.5 |
| Example 4 | 24.5 |
| Example 5 | 55 |
| Example 6 | 52 |
| Example 7 | 17 |
| | AUC of IB |
| Example 8 | 36 |
| Example 9 | 38 |
| Example 10 | 19 |
| Example 11 | 2.5 |

Assessment of In Vivo MCHR Activity in Young Growing Rats

Male SPRAGUE DAWLEY® (CD, Charles River Breeding Laboratory) rats weighing approximately 240 grams were place in individual plastic cages with ALPHADRI® bedding.

have revealed that rats exhibit a high preference for the high fat/high sucrose dies (80% preference). Body weight and consumption of both kinds of food as well as water intake were measured daily. Water was available ad lib throughout the study. Food consumption is presented as daily caloric consumption which is the sum of grams of chow multiplied by the Kcal per gram (3.5) plus grams of high fat high sugar multiplied by Kcal per gram (4.59).

Baseline body weight was measured prior to drug treatment on day 0 of the study. Baseline food consumption was the average of the 3 days prior to the first drug treatment. Drug was administered daily p.o. at 2.0 ml/kg at 1500 hours beginning on day 0 and continuing daily through day 4 as a suspension in 0.5% methyl cellulose, 0.1% Tween 80 in water at 3.0, 10 and 30 mg/kg p.o. All data were evaluated using ANOVA and Fishers PLSD statistics.

| Biological Data | | |
|---|---|---|
| Example | Dose (mg/kg) | Weight Reduction versus Vehicle |
| 1A (Dosed as Example 4) | 3 | 2.6% |
| | 10 | 3.5% |
| | 30 | 6.4% |
| 1B (Dosed as Example 9) | 1 | 2.9% |
| | 3 | 4.5% |
| | 10 | 6.4% |
| | 30 | 7.9% |

Assessment of MCHR In Vivo Activity in Mature Obese Rats

Male rats, obtained from Charles River Laboratories weighing 250-300 g, were singly housed in plastic cages on a 12 hour light, 12 hour dark cycle with lights out at 1 pm. The animal room was maintained at 72 degrees F. and 50% humidity. The rats were made obese by giving them simultaneous access to two different diets, HARLAN TEKLAD® rat chow (standard chow) and Research Diets D12327 (a high fat, high carbohydrate, highly palatable diet). The Research Diets chow is comprised of 40% vegetable fat, 40% carbohydrate (sucrose) and 20% protein. The Harlan diet is comprised of 5% fat (soybean oil), 67% carbohydrate (starch) and 22% protein. The normal Harlan rat diet used contains 3.4 kcal/gram of diet, and Research Diet #12327 contains 4.59 kcal/gram. The rats were on the choice diet regime for 10 weeks in order to induce obesity. Once started on the choice diet regime the rats are maintained on it for the duration of the study. Baseline feeding and body weight were collected and used to sort animals into treatment groups. Mean rat weight at the start of the choice diet was 250 grams. The mean weight of the rats at the start of chronic dosing was 661.7±6.3 (mean±sem) grams.

Rats were dosed orally one hour before the start of the dark cycle. Body weight and food consumption were measured daily at the time of dosing. Food consumption was converted to Kcal consumed. Total Kcal consumed was determined by adding the Kcal consumed for each diet and this was determined by multiplying grams of each diet consumed times the Kcal/gram.

Locomotor activity of the animals was determined on day 2 of the study using an Opto-M3 system from Columbus Instruments, Columbus, Ohio. This measurement was performed immediately after indirect calorimetry assessments on day 2. Activity was monitored in the evening beginning at 3 pm and continued for 16 hours. Photobeam breaks over time were collapsed into 60 minute bins.

Respiratory quotient (RQ) and oxygen consumption ($vO_2$) were measured by indirect calorimetry using an Oxymax system from Columbus Instruments, Columbus, Ohio. Measurements were made on days 2 and 15 of the study. Rats were dosed and placed in individual chambers. Six measurements for each animal were made with 45 minutes between measurements. Measurements were started at 10:00 AM, with the onset of the dark cycle at 1 PM. Data was normalized to body surface area ($kg^{0.75}$). Oxygen consumption and respiratory quotient were analyzed for statistical significance using repeated measures ANOVA followed by simple effects analysis. An echo MRI from Echo Medical Systems, Houston, Tex. was used to determine body composition. Percent body fat was measured on day 29 of the study. Changes in percent body fat were determined; statistical significance was determined using ANOVA with posthoc comparison via Fischers PLSD.

| Biological Data | | |
|---|---|---|
| Example | Dose (mg/kg) | Weight Reduction versus Vehicle |
| 1A (Dosed as Example 3) | Vehicle | 0% |
| | 0.3 | 2.09% |
| | 1.0 | 3.90% |
| | 3.0 | 3.57% |
| | 10 | 8.42% |
| | 30 | 10.16% |
| 1B (Dosed as Example 9) | Vehicle | 0% |
| | 0.03 | 1.7% |
| | 0.1 | 3.2% |
| | 0.3 | 5.0% |
| | 1 | 6.6% |
| | 3 | 7.8% |

What is claimed is:

1. A compound according to the following formula IA or a pharmaceutically acceptable salt thereof:

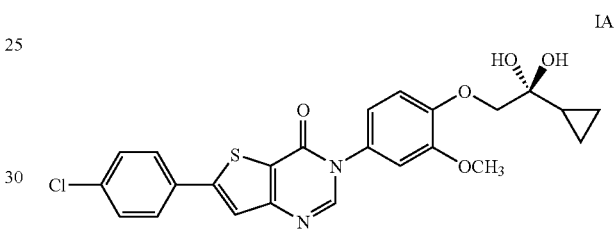

IA or a prodrug or stereoisomer thereof.

2. The compound according to claim 1 in the form of a prodrug ester or salt thereof selected from the group consisting of acetate, pivalate, methylcarbonate, benzoate, phosphate, and amino acid ester; or in the form of a prodrug ether or salt thereof selected from the group consisting of phosphate acetal and O-glucoside.

3. The compound according to claim 1 having one of the following structures, or a stereoisomer thereof:

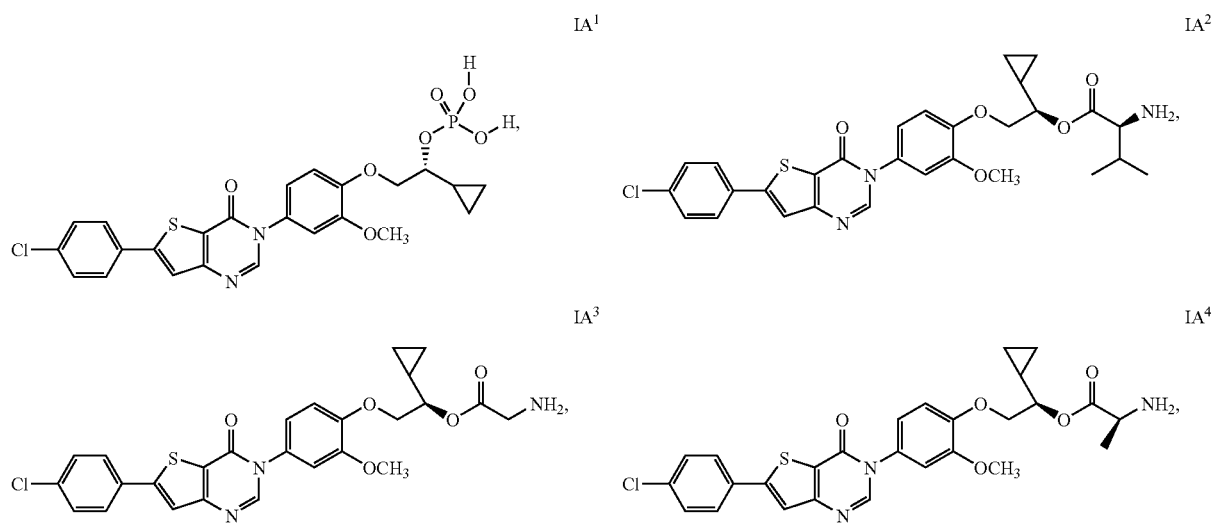

-continued

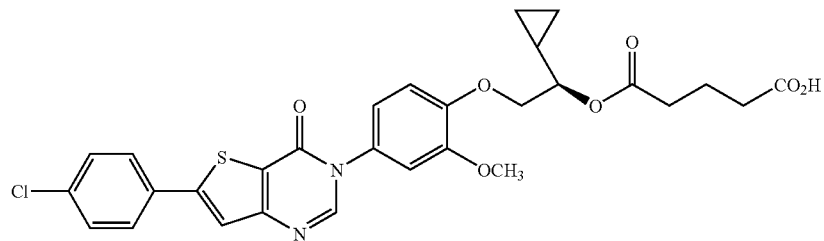

IA⁵ or a pharmaceutically acceptable salt of any of the foregoing structures.

4. A pharmaceutical combination comprising at least one compound according to claim 1 and at least one additional therapeutic agent selected from the group consisting of anti-obesity agents; anti-diabetic agents, appetite suppressants, anti-anxiety agents, anti-depressant agents, anti-inflammatory agents, cholesterol/lipid-lowering agents, and high-density lipoprotein (HDL)-raising agents.

5. The pharmaceutical combination according to claim 4 wherein said additional therapeutic agent is an anti-diabetic agent or an anti-obesity agent.

6. The pharmaceutical combination according to claim 5 wherein said additional therapeutic agent is a sodium-glucose transporter-2 (SGLT2) inhibitor.

7. A method for treating obesity comprising administering to a mammal in need of such treatment a therapeutically effective amount of a compound according to claim 1.

8. A compound of the structure

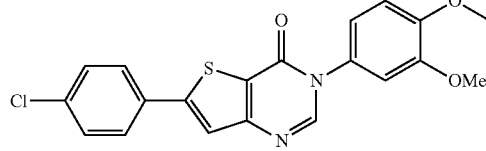

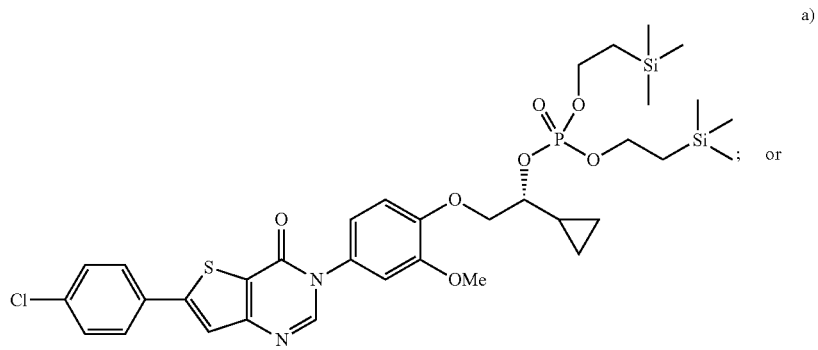

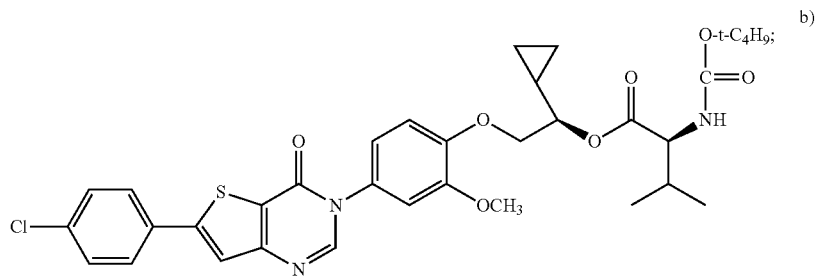

or a stereoisomer of any one of the foregoing structures.

9. A compound according to the following formula IA:

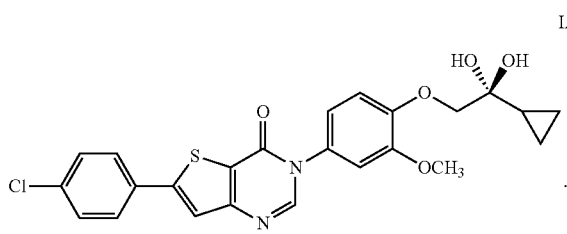

10. A compound according to the following formula IA¹:

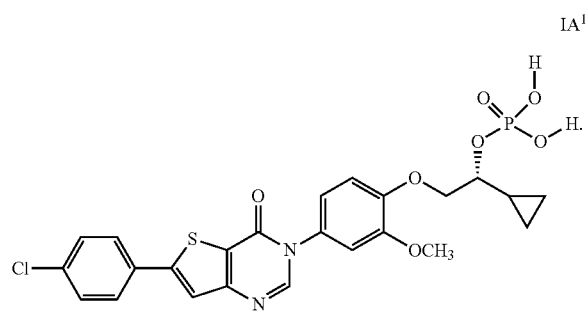

11. A pharmaceutical composition comprising at least one compound according to claim 9 and optionally at least one additional therapeutic agent selected from the group consisting of anti-obesity agents; anti-diabetic agents, appetite suppressants; cholesterol/lipid-lowering agents, anti-anxiety agents, anti-depressant agents, anti-inflammatory agents, and high-density lipoprotein (HDL)-raising agents together with at least one pharmaceutically acceptable diluent or carrier.

12. The pharmaceutical combination according to claim 11 wherein said additional therapeutic agent is an anti-diabetic agent or an anti-obesity agent.

13. The pharmaceutical combination according to claim 12 wherein said additional therapeutic agent is a sodium-glucose transporter-2 (SGLT2)inhibitor.

14. A pharmaceutical composition comprising at least one compound according to claim 10 and optionally at least one additional therapeutic agent selected from the group consisting of anti-obesity agents; anti-diabetic agents, appetite suppressants; cholesterol/lipid-lowering agents, anti-anxiety agents, anti-depressant agents, anti-inflammatory agents, and high-density lipoprotein (HDL)-raising agents together with at least one pharmaceutically acceptable diluent or carrier.

15. The pharmaceutical combination according to claim 10 wherein said additional therapeutic agent is an anti-diabetic agent or an anti-obesity agent.

16. The pharmaceutical combination according to claim 15 wherein said additional therapeutic agent is a sodium-glucose transporter-2 (SGLT21) inhibitor.

17. A method for treating obesity comprising administering to a mammal in need of such treatment a therapeutically effective amount of a compound according to claim 9.

18. A method for treating obesity comprising administering to a mammal in need of such treatment a therapeutically effective amount of a compound according to claim 10.

* * * * *

UNITED STATES PATENT AND TRADEMARK OFFICE
CERTIFICATE OF CORRECTION

PATENT NO. : 7,989,433 B2
APPLICATION NO. : 12/473346
DATED : August 2, 2011
INVENTOR(S) : William N. Washburn et al.

It is certified that error appears in the above-identified patent and that said Letters Patent is hereby corrected as shown below:

Column 16

Line 10, "(SGLT2)inhibitor." should read -- (SGLT2) inhibitor. --; and

Line 24, "(SGLT21)" should read -- (SGLT2) --.

Signed and Sealed this
Fifteenth Day of November, 2011

David J. Kappos
*Director of the United States Patent and Trademark Office*

UNITED STATES PATENT AND TRADEMARK OFFICE
CERTIFICATE OF CORRECTION

PATENT NO. : 7,989,433 B2  Page 1 of 1
APPLICATION NO. : 12/473346
DATED : August 2, 2011
INVENTOR(S) : William N. Washburn et al.

It is certified that error appears in the above-identified patent and that said Letters Patent is hereby corrected as shown below:

Column 56

Lines 25-33, " 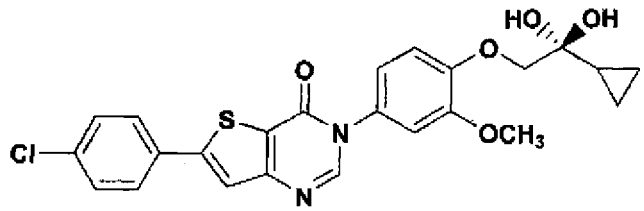 " should read

-- 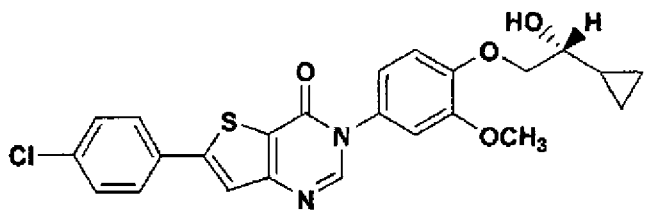 --.

Signed and Sealed this
Twenty-ninth Day of November, 2011

David J. Kappos
*Director of the United States Patent and Trademark Office*